US005740794A

United States Patent [19]
Smith et al.

[11] Patent Number: 5,740,794
[45] Date of Patent: Apr. 21, 1998

[54] APPARATUS AND METHODS FOR DISPERSING DRY POWDER MEDICAMENTS

[75] Inventors: Adrian E. Smith, Belmont; John D. Burr, Redwood City; Jeffrey W. Etter, Castro Valley; George S. Axford, Menlo Park; Jack M. Anthony, Palo Alto, all of Calif.

[73] Assignee: Inhale Therapeutic Systems, Palo Alto, Calif.

[21] Appl. No.: 487,184

[22] Filed: Jun. 7, 1995

Related U.S. Application Data

[63] Continuation-in-part of Ser. No. 309,691, Sep. 21, 1994.

[51] Int. Cl.$^6$ .......... A61M 15/00; A61M 16/00; B05D 7/14; B65D 83/06
[52] U.S. Cl. .......... 128/203.15; 128/203.21
[58] Field of Search .......... 128/200.22, 203.15, 128/203.21, 203.23, 203.24, 203.28, 202.22

[56] References Cited

U.S. PATENT DOCUMENTS

| 3,425,600 | 2/1969 | Abplanalp | 222/193 |
|---|---|---|---|
| 3,921,637 | 11/1975 | Bennie et al. | 128/203.15 |
| 3,991,761 | 11/1976 | Cocozza | 128/266 |
| 3,994,421 | 11/1976 | Hansen | 222/182 |
| 4,069,819 | 1/1978 | Valentini et al. | 128/206 |
| 4,105,027 | 8/1978 | Lundquist | 128/206 |
| 4,114,615 | 9/1978 | Wetterlin | 128/173 R |

(List continued on next page.)

FOREIGN PATENT DOCUMENTS

| 0347779 | 12/1989 | European Pat. Off. . |
|---|---|---|
| 0467172 | 1/1992 | European Pat. Off. . |
| 0468914 | 1/1992 | European Pat. Off. . |
| 0490797 | 6/1992 | European Pat. Off. . |
| 7712041 | 5/1979 | Netherlands . |
| 0628930 | 9/1978 | U.S.S.R. . |
| 1003926 | 3/1983 | U.S.S.R. . |
| 90/07351 | 7/1990 | WIPO . |
| 91/02558 | 3/1991 | WIPO . |
| 93/09832 | 5/1993 | WIPO . |
| 94/08552 | 4/1994 | WIPO . |

OTHER PUBLICATIONS

Chemical Engineers' Handbook, Fifth Edition, prepared under editorial direction of Robert H. Perry, Ejectors, pp. 6–29 through 6–32.

M. Bohnet, *Powder Technology*, 1984, pp. 302–313.

G.K. Budrick et al., *Chemical and Petroleum Engineering*, vol. 14, Nos. 9–10, Sep.–Oct. 1978.

L.S. Fox et al., *Powder and Bulk Engineering*, 1988, pp. 33–36.

A.N. Pittman et al., Solids Handling Conf. (1986), Paper 34, pp. C41–C51.

C.L. Witham et al., Wrkshp on Dissemination Techniques, Chemical Systems Lab., Aberdeen Proving Ground, MD, 1983.

V.M. Zholob et al., Translated from *Poroshkovaya Metallurgiya*, 1979, No. 6(198), pp. 13–16.

*Primary Examiner*—Kimberly L. Asher
*Attorney, Agent, or Firm*—Townsend and Townsend and Crew LLP

[57] ABSTRACT

A method for aerosolizing a powdered medicament comprises coupling a powder inlet end of a feed tube with a penetration in a receptacle containing the powder. Powder is drawn upward through the tube and dispersed in a high pressure gas stream flowing past a portion of the feed tube. Apparatus comprise the feed tube mounted within a base enclosure proximate a holder for one or more receptacles, which may be in the form of a cartridge containing a plurality of receptacles formed in a continuous web. The cartridge may be reciprocated relative to the feed tube and a separate piercing mechanism in order to sequentially piercing the receptacle and thereafter couple the feed tube through the resulting penetration for extracting the powder. Alternatively, penetration(s) through the receptacle may be formed as the feed tube is coupled, or some penetrations formed prior to coupling with other penetrations formed at the time of coupling.

32 Claims, 25 Drawing Sheets

U.S. PATENT DOCUMENTS

| | | | |
|---|---|---|---|
| 4,249,526 | 2/1981 | Dean et al. | 128/203 |
| 4,338,931 | 7/1982 | Cavazza | 128/203 |
| 4,446,862 | 5/1984 | Baum et al. | 128/203 |
| 4,627,432 | 12/1986 | Newell et al. | 128/203 |
| 4,807,814 | 2/1989 | Douche et al. | 239/428 |
| 4,811,731 | 3/1989 | Newell et al. | 128/203 |
| 4,884,565 | 12/1989 | Cocozza | 128/203 |
| 4,889,114 | 12/1989 | Kladders | 128/203 |
| 4,984,158 | 1/1991 | Hillsman | 128/202.22 |
| 4,995,385 | 2/1991 | Valentini et al. | 128/203 |
| 5,035,237 | 7/1991 | Newell et al. | 128/203 |
| 5,048,514 | 9/1991 | Ramella | 128/203 |
| 5,186,166 | 2/1993 | Riggs et al. | 128/203.15 |
| 5,201,308 | 4/1993 | Newhouse | 128/203.21 |
| 5,207,217 | 5/1993 | Cocazza et al. | 128/203.15 |
| 5,287,850 | 2/1994 | Haber et al. | 128/203.21 |
| 5,337,740 | 8/1994 | Armstrong et al. | 128/203.12 |
| 5,349,947 | 9/1994 | Newhouse et al. | 128/203.15 |
| 5,355,872 | 10/1994 | Riggs et al. | 128/200.21 |
| 5,388,572 | 2/1995 | Mulhauser et al. | 128/204.13 |
| 5,505,194 | 4/1996 | Adjei et al. | 128/203.23 |

APPARATUS AND METHODS FOR DISPERSING DRY POWDER MEDICAMENTS

CROSS-REFERENCE TO RELATED APPLICATIONS

This application is a continuation-in-part application of U.S. patent application Ser. No. 08/309,691, filed Sep. 21, 1994, pending, the disclosure of which is herein incorporated by reference.

BACKGROUND OF THE INVENTION

1. Field of the Invention

The present invention relates generally to methods and apparatus for the pulmonary delivery of drugs. More particularly, the present invention relates to a method and apparatus for dispersing dry powder medicaments for inhalation by a patient.

Effective delivery to a patient is a critical aspect of any successful drug therapy. Various routes of delivery exist, and each has its own advantages and disadvantages. Oral drug delivery of pills, capsules, elixirs, and the like, is perhaps the most convenient method, but many drugs are degraded in the digestive tract before they can be absorbed. Such degradation is a particular problem with modern protein drugs which are rapidly degraded by proteolytic enzymes in the digestive tract. Subcutaneous injection is frequently an effective route for systemic drug delivery, including the delivery of proteins, but enjoys a low patient acceptance. Since injection of drugs, such as insulin, one or more times a day can frequently be a source of poor patient compliance, a variety of alternative routes of administration have also been developed, including transdermal, intranasal, intrarectal, intravaginal, and pulmonary delivery.

Of particular interest to the present invention, pulmonary drug delivery relies on inhalation of a drug dispersion or aerosol by the patient so that active drug within the dispersion can reach the distal (alveolar) regions of the lung. It has been found that certain drugs are readily absorbed through the alveolar region directly into blood circulation. Pulmonary delivery is particularly promising for the delivery of proteins and polypeptides which are difficult to deliver by other routes of administration. Such pulmonary delivery is effective both for systemic delivery and for localized delivery to treat diseases of the lungs.

Pulmonary drug delivery (including both systemic and local) can itself be achieved by different approaches, including liquid nebulizers, metered dose inhalers (MDI's) and dry powder dispersion devices. Dry powder dispersion devices are particularly promising for delivering protein and polypeptide drugs which may be readily formulated as dry powders. Many otherwise labile proteins and polypeptides may be stably stored as lyophilized or spray-dried powders by themselves or in combination with suitable powder carriers. The ability to deliver proteins and polypeptides as dry powders, however, is problematic in certain respects. The dosage of many protein and polypeptide drugs is often critical so it is necessary that any dry powder delivery system be able to accurately, and precisely (repeatedly) deliver the intended amount of drug. Moreover, many proteins and polypeptides are quite expensive, typically being many times more costly than conventional drugs on a per-dose basis. Thus, the ability to efficiently deliver the dry powders to the target region of the lung with a minimal loss of drug is critical. It is further desirable that powder agglomerates present in the dry powder be sufficiently broken up prior to inhalation by the patient to assure effective systemic absorption or other pulmonary delivery.

A particularly promising approach for the pulmonary delivery of dry powder drugs utilizes a hand-held device with a pump or other source of pressurized gas. A selected amount of the pressurized gas is abruptly released through a powder dispersion device, such as a Venturi tube, and the dispersed powder made available for patient inhalation. While advantageous in many respects, such hand-held devices are problematic in a number of other respects. The particles being delivered are very fine, usually being sized in the range from 1 µm to 5 µm, making powder handling and dispersion difficult. The problems are exacerbated by the relatively small volumes of pressurized gas, typically 2 ml to 25 ml at 20 to 150 psig, which are available in such devices. In particular, Venturi tube dispersion devices are unsuitable for difficult-to-disperse powders when only small volumes of pressurized gas are available. Moreover, Venturi tube dispersion devices have very small powder inlet orifices which are easily plugged by the powders used for pulmonary delivery. Another requirement for hand-held and other powder delivery devices is high dosage concentration. It is important that the concentration of drug in the bolus of gas be relatively high to reduce the number of breaths and/or volume of each breath required to achieve a total dosage. The ability to achieve both adequate dispersion and small dispersed volumes is a significant technical challenge.

It would therefore be desirable to provide methods and systems for the dispersion of dry powder protein, polypeptide, and other drugs which meet some or all of the above objectives.

2. Description of the Background Art

Dry powder dispersion devices for medicaments are described in a number of patent documents. U.S. Pat. No. 3,921,637 describes a manual pump with needles for piercing through a single capsule of powdered medicine. The use of multiple receptacle disks or strips of medication is described in EP 467172 (where a reciprocatable piercing mechanism is used to piercing mechanism through opposed surfaces of a blister pack); WO91/02558; WO93/09832; WO94/08522; U.S. Pat. Nos. 4,627,432; 4,811,731; 5,035,237; 5,048,514; 4,446,862; and 3,425,600. Other patents which show puncturing of single medication capsules include U.S. Pat. Nos. 4,338,931; 3,991,761; 4,249,526; 4,069,819; 4,995,385; 4,889,114; and 4,884,565; and EP 469814. WO90/07351 describes a hand-held pump device with a loose powder reservoir.

A dry powder sonic velocity disperser intended for industrial uses and very high flow rates is described in Witham and Gates, *Dry Dispersion with Sonic Velocity Nozzles*, presented at the Workshop on Dissemination Techniques for Smoke and Obscurants, Chemical Systems Laboratory, Aberdeen Proving Ground, Md., Mar. 14–16, 1983.

A pneumatic powder ejector having a suction stage and an injection stage is described in U.S. Pat. No. 4,807,814. The device comprises an axial gas Venturi tube and a lateral powder inlet.

Pittman and Mason (1986), Solids Handling Conference, Paper C4, pages C-41 to C-51, describes an ejector nozzle (FIG. 2) having an annular air inlet upstream of a venturi restriction.

SU 628930 (Abstract) describes a hand-held powder disperser having an axial air flow tube.

SU 1003926 (Abstract) describes a gas thermal coating injector.

Budrik and Zhelonkina (1978), "Ejector Feeders for Pneumatic Transport Systems," in *Chemical and Petroleum*

*Engineering*, Consultants Bureau, New York, describes differing efficiencies in several ejector designs.

Zholob and Koval (1979), Poroshkovaya Metallurgiya 6:13-16, describes effects of injector design on particle size.

Bohnet (1984) "Calculation and Design of Gas/Solid-Injectors," in *Powder Technology*, pages 302-313, discusses conventional injector design.

Fox and Westaway (1988) Powder and Bulk Engineering, March 1988, pages 33-36, describes a venturi eductor having an axial air inlet tube upstream of a venturi restriction.

NL 7712041 (Abstract) discloses an ejector pump which creates suction and draws powder into a separator.

EP 347 779 describes a hand-held powder disperser having a collapsible expansion chamber.

EP 490 797 describes a hand-held powder disperser having a spring-loaded piston, where the piston carries a dispersion nozzle.

U.S. Pat. No. 3,994,421, describes a hand-held powder disperser having a collapsible deceleration chamber.

Pulmonary drug delivery is described in Byron and Patton (1994) J. Aerosol Med. 7:49-75.

SUMMARY OF THE INVENTION

The present invention provides methods and apparatus for efficient pulmonary delivery of accurate, precise, and repeatable dosages of powdered medicaments. The present invention will be particularly useful for the delivery of costly biopharmaceuticals such as protein, polypeptide and polynucleic acid drugs, but will also be useful for the systemic or localized delivery of any powdered medicament through the lungs. The delivery system and method produce substantially complete dispersion of the medicament powder with the break-up of any agglomerates of the powder which may have formed prior to delivery. The method and apparatus will find particular use in the dispersion of finely powdered medicaments from unit dosage receptacles, such as blister packs or cartridges, where the present invention is able to fluidize and extract substantially the entire amount of powder (usually at least 70% by weight, more usually at least 80%, and preferably at least 90%) within the receptacle, thus minimizing waste and enhancing the accuracy and precision of the dosage. The methods and approaches, however, will also find use with the dispersion and delivery of preselected metered amounts (boluses) of powdered medicaments from receptacles containing multiple dosage units, i.e. "bulk" powders contained in a single receptacle.

The methods and apparatus of the present invention are particularly suitable for the delivery of powders formed from discrete particles in the size range from 1 μm to 5 μm. Such powders, when properly dispersed in an aerosol, are optimum for delivery into the alveolar regions of the lung. However, they are particularly difficult to handle, and frequently become highly agglomerated during processing, packaging, and handling. Heretofore, handling characteristics of such powders have often been enhanced by combining the fine drug particles with larger carrier particles which have easier handling and dispersion characteristics. Use of a carrier, however, dilutes the drug, requiring a larger dispersion volume for a given drug dosage. The carrier particles can also cause choking when inhaled and serve no purpose other than improving handling characteristics. The present invention is able to achieve dispersion of fine drug particles with little or no carrier substances by a two-step dispersion method. The present invention, however, will be functional with drug compositions which include such carrier particles, as well as with diluents which may be necessary to achieve desired dosage concentrations.

The powders are first fluidized within the receptacle, as described above, resulting in fluidized particles and particle agglomerates which are then dispersed in the high velocity gas stream under conditions which break up such agglomerates. Such complete dispersion can be achieved with very low volumes of high velocity air and fluidization air, resulting in a well dispersed drug bolus having relatively high drug particle concentrations. Of course, the present invention is useful as well with drug formulations including a carrier diluent, or the like. The advantage of the present invention is that the use of carriers can often be reduced or eliminated altogether.

According to the method of the present invention, the powdered medicament is contained in a receptacle having a puncturable lid or other access surface. A powder inlet end of a feed tube is coupled with, i.e. engaged against or inserted through, a penetration in the access surface, and a high velocity airstream (usually sonic which provides sufficient shear forces to separate agglomerates into individual particles) is flowed past a portion of the tube, such as an outlet end, to draw powder from the receptacle, through the tube, and into the flowing airstream to form the desired aerosol. Usually, at least two spaced-apart discrete penetrations will be formed in the access surface prior to coupling the inlet end of the feed tube with one of the penetrations. The other penetration permits a separate stream of fluidization air to enter the receptacle, fluidize the powder, and sweep the receptacle of the fluidized powder to help assure that substantially all powder (preferably at least 70%, more preferably at least 80%, and still more preferably at least 90%) is removed into the flowing air stream. The high pressure gas stream will be generated by abruptly releasing a charge of pressurized gas through a flow path which intersects with the outlet end of the feed tube at an angle selected to both (1) induce sufficient fluidization air flow through the feed tube to fluidize and transport powder in the receptacle and (2) break up powder agglomerates which remain as the powder exits from the outlet end of the feed tube. The gas pressure prior to release will usually be at least about 15 psig (to achieve sonic velocity), preferably being at least 20 psig, and more preferably being in the range from 20 psig to 150 psig, and usually being in the range from 40 psig to 80 psig. The expanded volume of released gas (measured at standard temperature and pressure (STP) of 14.7 psig and 20° C.) will thus usually be in the range from 2 ml to 25 ml, preferably being from 4 ml to 15 ml. Release of the high pressure gas can be effected by a manual trigger or optionally by sensing negative pressure resulting from the patient's inspiration (i.e., can be breath-activated). As described in detail below, the high pressure gas stream will combine with the fluidization air stream at a volume ratio (measured at STP) in the range from 1:2 to 1:4 (high pressure gas: fluidization air) to produce the aerosol which is subsequently inhaled by the patient, optionally after capture in a plume capture chamber.

The method may further comprise the step of capturing the resulting discrete volume of aerosolized powder in a plume capture chamber prior to subsequent inhalation by the patient. The patient is then able to inhale the entire aerosolized dose from the chamber, concurrently with and/or followed by inhalation of ambient air which sweeps the capture chamber to further assure efficient delivery of the powder with minimum losses. Inhalation of chase air following the initial bolus of medication will drive the medication deep into the alveolar regions of the lung where absorption will occur. The method optionally further comprises advancing a plurality of powder-containing receptacles past the feed tube, typically in the form of a strip or disk, so the powder can be sequentially drawn and dispersed from each receptacle.

In another aspect of the method of the present invention, discrete quantities of a powdered medicament may be sequentially delivered from a receptacle or reservoir. In contrast with the previously described methods, the receptacle will include an amount of powdered medicament which is larger than that intended to be delivered in any single bolus, usually containing an amount which is sufficient for a large number of boluses, usually at least 5, preferably at least 10, and frequently 20 or more. The method comprises inserting the inlet end of the feed tube into the receptacle and flowing a high pressure gas stream past an outlet end of the feed tube to induce airflow from the receptacle through the tube. The powdered medicament is thus entrained in the airflow passing through the feed tube and combined with the high pressure gas stream at an outlet end of the feed tube. The high pressure gas stream can be repeatedly directed past the outlet end of the feed tube while the inlet end remains within the "bulk" powdered medicament receptacle.

Apparatus according to the present invention comprise a base enclosure having a support for the powder-containing receptacle at a fluidization location. The feed tube is mounted within the base enclosure and a mechanism for reciprocating the receptacle relative to the feed tube (or extending the feed tube relative to the receptacle) is optionally provided. A source of compressed gas for generating the high pressure gas is also provided, typically in the form of a hand-actuated pump, an electric (usually battery-operated) pump, a compressed gas container, a two-fluid system, or the like. The aerosolized powder dosage may thus be formed by reciprocating the receptacle relative to the feed tube so that the inlet end of the tube enters the receptacle. The high pressure gas stream is released while the tube is in or adjacent to the receptacle, and the resulting low pressure region at the outlet end of the feed tube draws fluidization air into the receptacle (preferably from the plume capture chamber which subsequently receives the aerosol, thus minimizing net air introduced from outside the device) to fluidize and extract the powder outward from the receptacle through the tube, and into the high velocity gas stream to form the desired dispersion. Usually, the capture chamber is disposed over and in-line with the outlet end of the feed tube to contain the "plume" of powder aerosol and allow the plume to quiesce prior to inhalation by the patient. The feed tube does not have jets or ejector tubes within the flow path, and the clear, undisrupted flow path reduces any tendency for the feed tube to clog or otherwise lose dispersion efficiency. Using air from the capture chamber as a source of fluidization gas is advantageous since it reduces the total volume of "new" gas introduced to the chamber, making capture of the dispersion gas stream (i.e., the combination of the high pressure gas stream and the fluidization air stream) easier. Such recycling of air from the capture chamber, however, is not an essential feature of the present invention. Fluidization air can also be obtained directly from outside the device.

In a particular aspect of the apparatus of the present invention, the receptacle will be supported in a mechanism for advancing a continuous web (e.g. a strip or disk) which carries a plurality of receptacles past the fluidization location. Usually, the web advance mechanism includes a cartridge or carriage which holds the web and which is reciprocatably mounted relative to the feed tube so that the receptacles may be sequentially advanced while the cartridge and tube are separated, and the tube thereafter introduced into the receptacle by moving the cartridge and tube together. Optionally, the receptacle lid or other single access surface (i.e., a surface on one side of the receptacle) will be pierced immediately prior to introduction of the feed tube, usually using a separate piercing mechanism which pierces the lid as the cartridge is reciprocated relative to the feed tube. Alternatively, the access surface can be pierced simultaneously with the insertion of the feed tube. In the latter case, the inlet end of the feed tube will usually have a piercing structure and/or additional piercing structures will be provided to form additional penetrations for the entry of the fluidization air.

In a specific aspect of the apparatus of the present invention, the piercing mechanism will produce at least two spaced-apart holes in the lid, where one hole receives or engages the feed tube and the other hole(s) permit entry of displacement air to fluidize the powder and sweep the receptacle as powder is withdrawn through the feed tube. A conduit or other path may also be provided for directing air from the plume capture chamber back to the receptacle in order to at least partially provide the necessary displacement air. The hole for the feed tube may be formed simultaneously with or at a different time from the displacement air hole(s). For example, the displacement air hole(s) could be formed at a piercing station disposed ahead of the dispersion station with the feed tube hole formed at the dispersion station, or vice versa. It also may be desirable to provide a piercing mechanism at the dispersion station where the feed tube piercing structure is reciprocated relative to the receptacle in a separate motion from the displacement air hole piercing structure.

The present invention further provides apparatus for aerosolizing of powder comprising a feed tube having an inlet end, an outlet end, and a lumen defining an axial flow path between said inlet end and outlet end. At least one conduit is provided for flowing a high velocity gas stream past the outlet end in a direction which converges with the axial flow path at an angle in the range from 12.5° to 65°. It has been found that the angle of convergence in this range induces a sufficient flow of fluidization air in the feed tube to efficiently empty an associated powder receptacle (typically removing and aerosolizing at least 80% and preferably at least 90% of the powder initially present in the receptacle) while also providing sufficient shear energy at the outlet end to substantially break up agglomerates which are present in the powder.

The aerosolizing apparatus may include two or more separate gas conduits which converge from different, usually opposite (diametrically opposed), sides of the flow path. Alternatively, the high pressure gas conduit may terminate in a single annular aperture which circumscribes the outlet end of the feed tube and which creates a gas flow path which converges on the axial flow path. The latter approach however, will generally be less preferred since it is difficult to manufacture annular apertures in the small size required. The total lumen area ($A_1$) of the high pressure (dispersion) gas flow conduit(s) will usually be in the range from 0.05 $mm^2$ to 0.3 $mm^2$, while the throat of the feed tube immediately upstream of the gas conduit(s) tube will have a lumen area ($A_2$) in the range from 0.5 $mm^2$ to 10 $mm^2$. The area ($A_3$) and length of the mixing volume immediately downstream from the high velocity gas conduits are preferably in the range from the 0.6 $mm^2$ to 11 $mm^2$ and 0.5 mm to 3 mm, respectively. The feed tube upstream of the throat will usually have an area ($A_4$) in the range from 0.6 mm$^2$ to 15 mm$^2$.

The aerosolizing apparatus may further include a diffuser tube extending from the outlet end of the mixing volume and having a lumen which is usually but not necessarily coaxially aligned with the feed tube lumen. The diameter of the diffuser tube lumen will increase in a direction away from the outlet end of the mixing volume, typically diverging at a half angle of 2° to 10° over a length in the range from 0.5 cm to 5 cm, usually having an outlet area which is about four times the inlet (mixing volume) area. The diffuser tube thus causes a reduction in the velocity of the gas stream exhausted from the outlet end of the mixing volume, where velocity is at a maximum, prior to entering the plume capture chamber plum plume continues to slow rapidly as it expands within the chamber and approaches a quiet or quiescent state prior to inhalation.

The present invention further provides a feed tube assembly comprising a casing, a flow-directing member, and a feed tube. The assembly is replaceable within the aerosol dispersion system, facilitating removal and cleaning or exchange of the assembly if it becomes plugged or fouled.

The invention provides an improved apparatus for aerosolizing a powdered medicament. The apparatus is of the type having a housing and a source of pressurized gas for aerosolizing the powder. Such an apparatus is improved by providing a pressurization cylinder, a piston slidable within the cylinder, and a release valve in communication with the cylinder. Further provided is a handle assembly having a handle operably attached to the piston and a means for closing the valve. In this manner, translation of the handle closes the valve and axially translates the piston within the cylinder to produce the pressurized gas.

In one aspect, the release valve comprises a valve stem connected to a valve poppet, and the means for closing the valve comprises a roller cam adjacent the valve stem for translating the valve stem to close the valve as the handle is translated radially outward from the housing. In another aspect, the handle assembly further includes a toggle link which moves over-center to hold the roller cam against the valve stem and keep the valve closed. In this way, the valve is held closed while the piston is translated back toward the housing to produce the pressurized gas. In a further aspect, the handle assembly includes a linkage between the handle and the piston. In this manner, the linkage reciprocally translates the piston between a retracted position and a charged position within the cylinder as the handle is translated radially outward and radially inward relative to the housing. With such a configuration, the handle may be moved radially outward to both close the valve and retract the piston, while inward movement of the handle charges the cylinder with pressurized gas.

In yet another aspect, an interlocking means is provided for preventing inward radial translation of the handle until the toggle link has moved over-center to hold the valve closed. Preferably, the interlocking means comprises a rack and a pawl. In a further aspect, a release button is provided for translating the roller cam from the over-center position to open the valve. In yet a further aspect, the cylinder preferably includes a one-way valve for allowing air to enter the cylinder as the piston is translated to the retracted position.

In one particular aspect, the powdered medicament is held within a receptacle. A feed tube is provided having an inlet end, an outlet end, and a lumen extending therebetween so that the inlet end may be inserted into the receptacle. In this way, compressed gas exiting the release valve may be flowed past the outlet end of the feed tube, with powder from the receptacle being extracted through the tube and dispersed in the flowing compressed gas to form the aerosol. Preferably, a means is provided for piercing at least one hole in an access surface of the receptacle simultaneously with inserting the inlet end of the feed tube into the receptacle. In a preferable aspect, the piercing means comprises a pair of pointed tabs, with the tabs being each disposed at an oblique angle relative to the access surface of the receptacle when the tabs are pierced through the access surface.

In another particular aspect, a means is provided for reciprocally translating the receptacle toward and away from the piercing means. The translating means preferably includes an over-center linkage for locking the receptacle in place upon insertion of the inlet end of the feed tube into the receptacle. In another aspect, a positioning pin is provided for aligning the receptacle in a preferred orientation relative to the piercing means while inserting the inlet end of the feed tube into the receptacle.

In yet another particular aspect, the handle assembly includes four linkages for attaching the handle to the housing. In this manner, the handle may be translated radially outward and radially inward relative to the housing with a generally constant force, and with a more linear motion than with a simple pivot. Further, such linkages reduce the distance that the handle must be translated away from the housing, thereby making easier hand operation of the handle assembly. In another aspect, a means is provided on or in association with the housing for producing verbal operating instructions.

The invention provides an exemplary apparatus for aerosolizing a powder held in a receptacle having a puncturable access surface. The apparatus includes a housing, a source of pressurized gas, a capture chamber attached to the housing, and a TRANSJECTOR™ multi-flow ejector assembly removably held within the housing. The TRANSJECTOR™ multi-flow ejector assembly includes a means for piercing the access surface of the receptacle and for receiving pressurized gas to draw powder from the receptacle and into the capture chamber. In a preferable aspect, the TRANSJECTOR™ multi-flow ejector assembly receives gas directly from the gas source and delivers powder directly to the capture chamber without powder passing through other portions of the apparatus.

In a particular aspect, an interface seal is provided between the TRANSJECTOR™ multi-flow ejector assembly and the housing so that pressurized gas may be passed from the housing to the TRANSJECTOR™ multi-flow ejector assembly without substantial loss of the gas. Preferably, the interface seal is angled relative to a central axis of the TRANSJECTOR™ multi-flow ejector assembly to facilitate easy removal of the TRANSJECTOR™ multi-flow ejector assembly from the housing. In another aspect, a receptacle seal is provided for forming a seal between the TRANSJECTOR™ multi-flow ejector and the receptacle. In a further aspect, the TRANSJECTOR™ multi-flow ejector assembly is keyed to be repeatedly received into the housing in a unique orientation.

In another particular aspect, the capture chamber is axially slidable over the housing so that the capture chamber may be placed in a collapsed position substantially covering the housing or an extended position forming an enclosure for receiving aerosolized powder. Preferably, at least one detent is provided in the housing and at least one notch is provided in the capture chamber, with the detent being received into the notch when the capture chamber is in the extended position. A spring is preferably provided for outwardly biasing the detent. In another aspect, the detent is generally V-shaped in geometry. In a further aspect, the capture chamber comprises an elongate chamber body having at least one elongate ridge or rib extending longitudinally along the body. The elongate ridge engages the housing when the chamber is collapsed to limit the amount of accumulated powder on the chamber that may be scraped from the chamber by the housing. In yet another aspect, the chamber body is asymmetrical in cross-sectional geometry and includes a mouthpiece. A cap is preferably removably held over the mouthpiece to prevent external dust and particulate from entering the chamber and to hold the powdered medicament within the chamber until ready to be inhaled. A seal is preferably provided between the cap and the mouthpiece, with the seal preferably being configured to function as a bleed valve to allow excess gas within the chamber to escape.

The invention further provides a receptacle for holding a powdered medicament, with the receptacle being adapted to be received into a housing of an aerosolizing apparatus. The receptacle includes a receptacle body having a puncturable access surface and a tab extending from the receptacle body. In this manner, the receptacle body may be received into an aperture in the housing with at least a portion of the tab remaining outside the housing. In one aspect, the tab includes a keyed hole adapted to receive an alignment pin in the aerosolizing apparatus. By keying the hole in the tab, the receptacle may be configured so that it may only be used with an apparatus having a mating alignment pin. In this way, the apparatus may be configured to receive only certain receptacles having a particular medicament.

The invention provides an improved method for aerosolizing a powdered medicament. The method is of the type wherein the powder is entrained and suspended in a flowing gas stream and comprises providing a housing having a pressurization cylinder, a piston slidable within the cylinder, a release valve in communication with the cylinder, and a handle for axially translating the piston and for closing the release valve. The handle is initially translated away from the housing to axially translate the piston within the cylinder to a retracted position and to close the release valve. The handle is then translated back toward the housing to translate the piston to a position where it creates a charge of pressurized gas. The valve is released following charging to abruptly discharge the pressurized gas.

In one particular aspect, translation of the handle in the direction of the housing is prevented until the release valve is closed. In this way, premature introduction of gas to the medicament is prevented until the cylinder is fully charged. In another aspect, the release valve is held closed while translating the handle back toward the housing so that gas in the cylinder may be charged by the piston. In a further aspect, the handle is kept generally parallel to the housing when translated. Preferably, the handle is translated toward the housing to pressurize the gas while applying a generally constant force to the handle.

In another particular aspect, the powder that is suspended in the released gas is introduced into a capture chamber while simultaneously bleeding off a preselected amount of gas from the capture chamber. In still another aspect, a TRANSJECTOR™ multi-flow ejector assembly is provided for receiving the pressurized gas and aerosolizing the powder. The TRANSJECTOR™ multi-flow ejector assembly is removably held in the housing so that it may periodically be removed from the housing for cleaning. In yet another aspect, verbal operating instructions are produced from the housing.

In still another particular aspect, a receptacle having a puncturable lid is provided for holding the medicament. The receptacle is translated toward the TRANSJECTOR™ multi-flow ejector assembly until the TRANSJECTOR™ multi-flow ejector assembly penetrates the lid. Preferably, the receptacle is guided toward the TRANSJECTOR™ multi-flow ejector so that the TRANSJECTOR™ multi-flow ejector penetrates the lid at a known and a predictable position. The receptacle is preferably held with the TRANSJECTOR™ multi-flow ejector assembly penetrating its lid until after the valve is released.

The invention provides an exemplary method for aerosolizing a powdered medicament. According to the method, receptacles are provided having a receptacle body and a tab extending from the receptacle body, with the powdered medicament being held within the receptacle bodies. One of the receptacles is inserted into a housing having an aperture, with the receptacle body being received within the aperture so that at least a portion of the tab remains outside the housing. The receptacle body is raised and simultaneously pierced and the powdered medicament in the receptacle is extracted in a gas stream that can be inhaled. The receptacle is lower, and the tab is then pulled to remove the receptacle from the housing.

In one aspect, the housing has a reciprocatable capture chamber for receiving the powder-bearing gas stream, and the chamber is preferably deployed prior to inserting the receptacle. Deploying of the chamber exposes the aperture, and insertion of the receptacle into the aperture prevents the chamber from retracting until the receptacle is removed.

DESCRIPTION OF THE SPECIFIC EMBODIMENT

Figure 1:
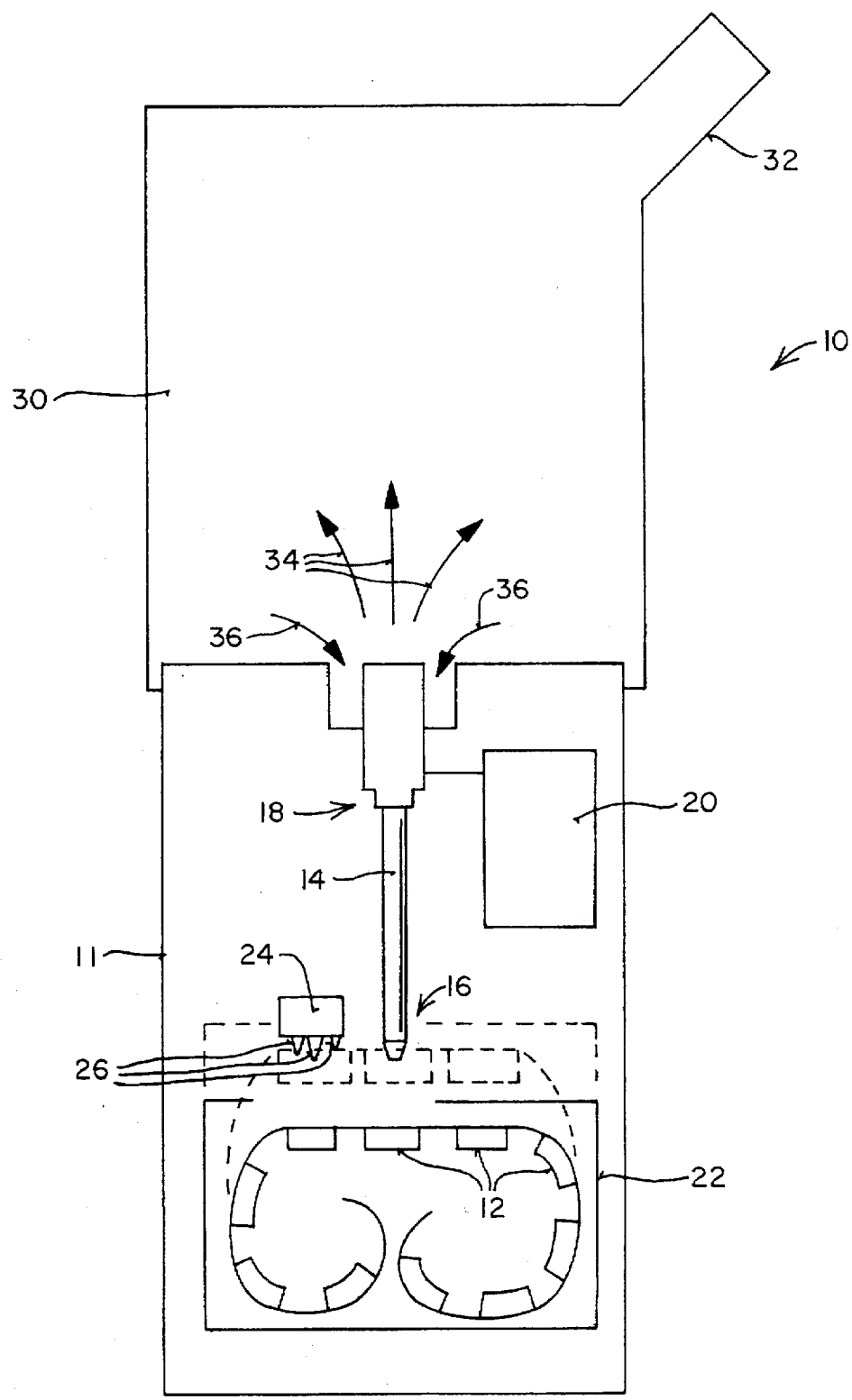
FIG. 1 is a schematic illustration of an aerosol dispersion system constructed in accordance with the principles of the present invention.

Referring now to FIG. 1, a system 10 for dispersing a powder medicament from a plurality of receptacles 12 by insertion of a feed tube assembly 14 will be described. The receptacles may be in any form that holds and preserves the medicaments and which provides a puncturable access surface. As illustrated, receptacles 12 are in a continuous web comprising individual wells covered by a puncturable lid, typically a metal foil or other conventional laminate. Each receptacle will include a precise dosage of the powdered medicament to be delivered. The amount of powder in each individual receptacle will usually be in the range from about 1 mg to 20 mg, more usually being from 2 mg to 10 mg. The continuous web may be in the form of a strip, disk, or molded structure with a closure. The manufacture of such containers, often referred to as "blister packs" is well known in the pharmaceutical packaging art and need not be described further.

Although illustrated with cartridge 22 in FIG. 1, it will be appreciated that the powder dispersion systems of the present invention could also be constructed to receive single dosage packages carrying only one receptacle. In such a case, the user would insert the package so that the receptacle was properly oriented relative to feed tube 40 (FIG. 2) of feed tube assembly 14. Necessary piercings in the access surface of the receptacle could be made manually prior to insertion, could be made within the system 10 (either prior to or simultaneous with introduction of the feed tube assembly 14) or could be preformed and exposed by peeling away a cover prior to insertion of the package into the device. Multiple receptacle packages could also be provided where the package is inserted into the device at different orientations in order to selectively expose individual receptacles to the feed tube. A variety of design options are available when the user inserts a single receptacle prior to each use.

The system 10 further comprises a base enclosure 11, and the feed tube 40 (FIG. 2) of feed tube assembly 14 has an inlet end 16 and an outlet end 18. A pressurized gas source 20 is provided within the base enclosure 11 and is connected to the proximal end of the feed tube assembly 14 to provide a high pressure gas stream, as will be described in greater detail in connection with FIG. 2.

The receptacles 12 will be mounted within the base enclosure 11 to reciprocate relative to the inlet end 16 of feed tube assembly 14. Preferably, the strip of receptacles 12 will be mounted within a cartridge 22 which is reciprocatably mounted in the base enclosure 11, while the feed tube assembly 14 is fixedly mounted within the base enclosure. In this way, the receptacles 12 may be sequentially advanced past a fluidization location (defined by the inlet end 16 of feed tube assembly 14) within the cartridge 22, with the receptacle which is at the dispersion or fluidization location being brought proximate the inlet end 16 of the feed tube to permit emptying of its powdered contents, as described in more detail hereinafter. Both reciprocation of the cartridge 22, and advance of the receptacles 12 within the cartridge, may be accomplished manually by the user. Alternatively, a mechanism may be provided within the base enclosure 11 for simultaneously reciprocating the cartridge 22 and advancing the strip of receptacles 12, either as part of a manual advance mechanism or as part of a battery-powered mechanism.

Figure 3:
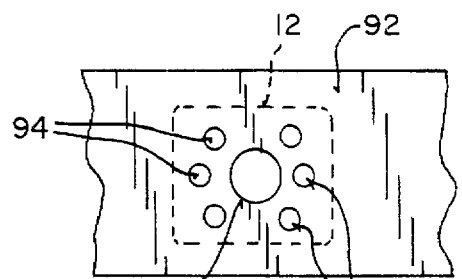
FIG. 3 illustrates a preferred powder receptacle lid penetration pattern.

In the embodiment of FIG. 1, penetrations will be formed in the lid of the strip of receptacles 12 by a piercing mechanism 24. As illustrated, the piercing mechanism 24 will be fixedly mounted within the base enclosure 11 and will include a plurality of sharpened penetrating elements 26 disposed to contact and penetrate the puncturable lid 92 (FIG. 3) of the receptacles 12 when the cartridge 22 is reciprocated, as illustrated in broken line in FIG. 1. The piercing mechanism 24 will be located to contact a receptacle 12 which is located one station prior to the feed tube assembly 14. Thus, each receptacle 12 will be pierced immediately prior to being advanced to the fluidization location.

It will be appreciated that a wide variety of mechanisms can be provided for piercing holes within the lid of each receptacle and for bringing the receptacle into proximity with the feed tube assembly 14. For example, the cartridge 22 could be held stationary within the base enclosure 11 while each of the feed tube assembly 14 and piercing mechanism 24 could be reciprocated, either together or separately. Alternatively, the inlet end 16 of the feed tube assembly 14 could be configured to be self-penetrating (see FIGS. 10 and 11A and 11B below). In the latter case, the desired pattern of penetrations would be formed in the puncturable lid of the receptacle 12 at the same time that the inlet end is engaged against or inserted into the interior of the receptacle. The present invention is not limited to any particular puncturing and advance mechanisms which might be employed.

The gas source 20 will provide a volume of high pressure air or other gas to the outlet end 18 of the feed tube 40 (FIG. 2) of feed tube assembly 14 in order to induce a flow of fluidization air, draw powder from the receptacles 12, and disperse the powder within the flowing gas stream. While the high velocity air from the gas source will usually be directed past the outlet end 18, it will be appreciated that feed tube 40 could be extended past the high velocity gas stream inlet point, for example by providing side inlets in an elongate tube. Thus, the high velocity gas could actually combine with the fluidization air carrying the entrained particles within the feed tube itself. With such a construction, the feed tube 40 could define the mixing volume 60 (FIG. 4A), as described below.

The gas source 20 will provide gas at a relatively high pressure, usually being sufficient to provide for sonic flow past the outlet end 18 of the feed tube assembly 14, typically being above 15 psig, usually being at least 20 psig, and preferably being in the range from 20 psig to 150 psig, and most preferably being in the range from 40 psig to 80 psig. The energy stored in the charge of high pressure gas will be sufficient to induce air flow through the feed tube 40 of feed tube assembly 14 which in turn draws fluidization air into the receptacle to fluidize and extract the expected weight of powdered medicament from the receptacle 12. The expanded volume of the charge will typically be in the range from about 2 ml to 25 ml (measured at STP), usually being in the range from about 4 ml to 15 ml. The volume of fluidization gas whose flow is induced through the feed tube assembly 14 by the high velocity gas stream will usually be from 2 ml to 100 ml, preferably from 4 ml to 60 ml, measured at STP. The specific manner in which the high pressure gas is flowed past the outlet end 18 of feed tube assembly 14 will be described in greater detail in connection with FIG. 2.

Gas source 20 may be in the form of a manual pump, an electric pump, a high pressure gas cylinder, or the like. The construction of manual pumps in hand-held powder dispersion devices is described in the patent and technical literature. See e.g., WO90/07351. The construction of electric gas pumps, gas cylinder supplies, and two-fluid systems is also well within the skill in the art.

The gas dispersion system 10 further includes a plume capture chamber 30 which is disposed over the outlet end 18 of feed tube assembly 14 in order to capture powder released from the tube. The plume chamber 30 will include a mouth piece 32 at its distal end and will have an internal volume sufficient to capture substantially all of the powder dispersion which is delivered from the feed tube assembly 14. Usually, the volume will be in the range from 50 ml to 1000 ml, preferably from 100 ml to 750 ml. The chamber 30 will also include an ambient air inlet (not shown), optionally a tangential inlet as described in co-pending Application Ser. No. 07/910,048, the full disclosure of which is incorporated herein by reference. Alternatively, the air inlet can be axial or spiral, as described in connection with FIGS. 7–9, below.

In operation, the powder dispersion will be introduced into the plume capture chamber 30, as illustrated by arrows 34. Air will be displaced through the mouthpiece 32, and optionally back through an annular lumen in the feed tube assembly 14, as indicated by arrows 36 and as will be described in more detail in connection with FIG. 2. Such recycling of air from the plume capture chamber 30 as the fluidization gas enters greatly reduces the total volume of new gas being introduced to the system. The only new gas introduced (prior to patient inhalation) will be from the gas source 20. After the entire contents of a receptacle 12 has been dispersed and captured within the plume chamber 30, the patient will inhale the entire aerosolized dose through the mouthpiece 32 chased by ambient air through the chamber to extract all aerosolized medicament from the chamber. Optionally, an orifice plate or other flow limiting element may be placed in the chamber air inlet path to slow inhalation and enhance the penetration depth of the powder particles. Inhalation of the additional air further assures that the powdered medicament will be efficiently dispersed and driven deeply into the alveolar regions of the lung where it is available for systemic absorption or localized delivery.

Figure 2:
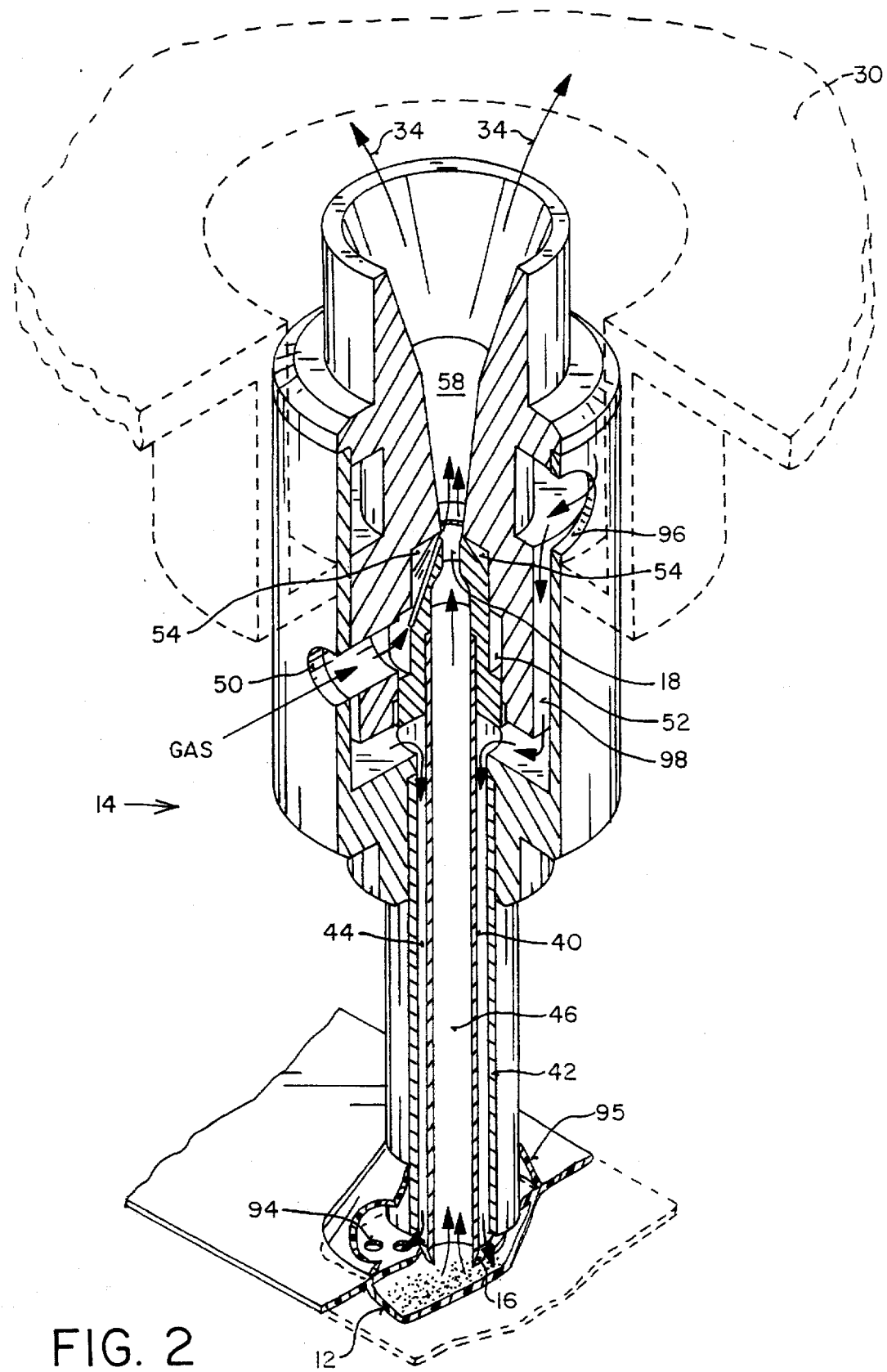
FIG. 2 is a perspective illustration of a powder feed tube assembly employed in the aerosol dispersion system of FIG. 1, shown in quarter-section with its inlet end proximate a powder receptacle.

Referring now to FIG. 2, the feed tube assembly 14 includes an inner tubular feed tube 40 which defines the inlet end 16 of the feed tube assembly 14 at its distal end and an outer coaxial tube member 42 which defines an annular lumen 44 for passing return air from chamber 30 back to the receptacle 12, as described in more detail hereinafter.

Lumen 46 of the inner tubular feed tube 40 extends from the inlet end 16 to the outlet end 18 where a throat or constriction is optionally formed. The throat or constriction is not necessary for operation of the feed tube assembly 14, but it is the area ($A_2$) at the outlet end of the lumen 46 (FIG. 4A) which determines the performance characteristics of the feed tube, as described in more detail hereinafter. Dispersion gas from gas source 20 enters the feed tube assembly 14 through a port 50 connected to an annular plenum 52. The annular plenum 52, in turn, is connected to a pair of gas conduits 54 which direct converging gas streams into the flow path defined by lumen 46 of the feed tube 40. The angle at which the gas conduits 54 are oriented is chosen to provide a proper balance between the magnitude of the flow velocity induced in the powder stream drawn through lumen 46 and the magnitude of the shear forces which break up agglomerates in the powder as they pass from the outlet end 18 into an expansion section 58.

The area ($A_2$) (FIG. 4A) of the throat 18 of the feed tube lumen 46 will typically be in the range from 0.5 mm$^2$ to 10 mm$^2$, preferably being in the range from 1 mm$^2$ to 4 mm$^2$. In the illustrated embodiment, area ($A_4$) of the upstream portion of lumen 46 (FIG. 4A) is greater than $A_2$, typically being from 0.6 mm$^2$ to 15 mm$^2$. The upstream lumen 46, however, could have a uniform area along its entire length equal to the outlet end area ($A_2$), although such a construction would be less preferred.

Figure 4A:
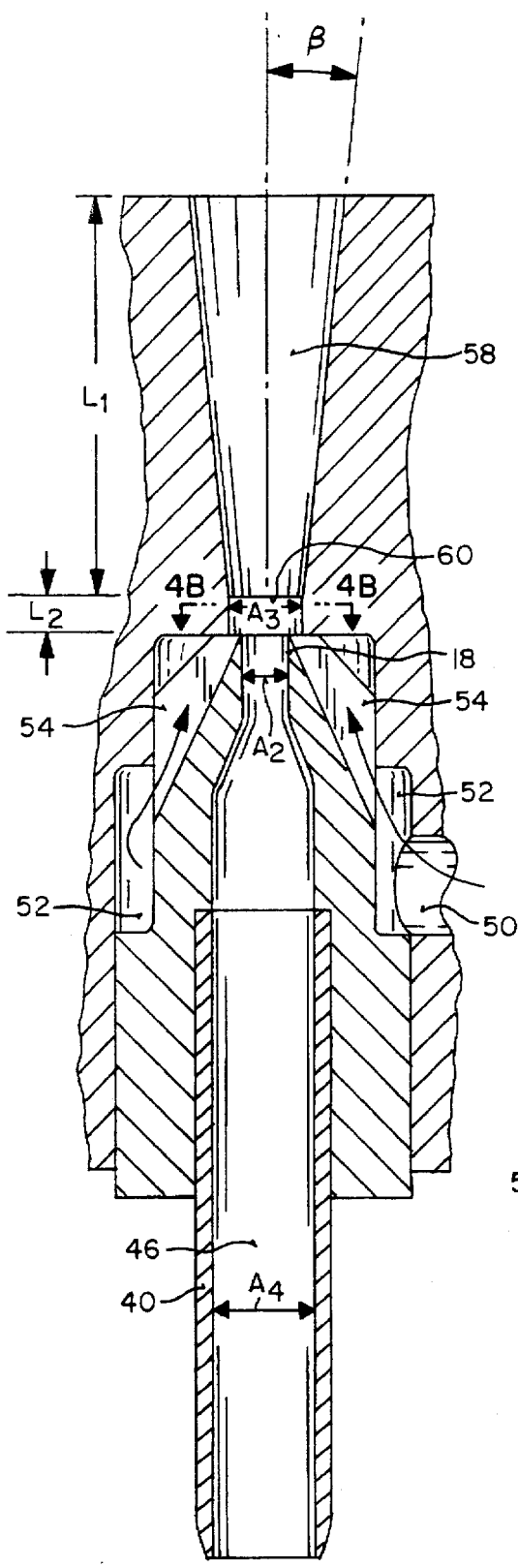
FIG. 4A is a cross-sectional view of a portion of the feed tube assembly illustrated in FIG. 2.
Figure 4B:
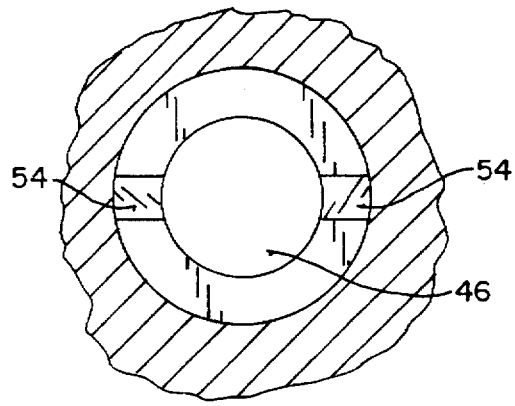
FIG. 4B is a cross-sectional view taken along line 4B—4B of FIG. 4A.
Figure 4C:
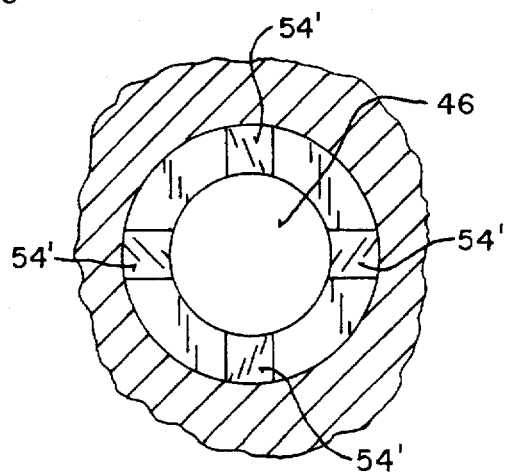
FIG. 4C is an alternative cross-sectional view taken along line 4B—4B of FIG. 4A.

Referring to FIG. 4A, a mixing volume 60 having a uniform (non-expanding) cross-sectional area ($A_3$) and a length ($L_2$) is located immediately at the outlet end 18 of the feed tube 40. The cross-sectional area ($A_3$) is shown to be slightly larger than feed tube throat area ($A_2$) outlet, but this is not necessary. The exemplary area ($A_3$) is typically in the range from 0.6 mm² to 11 mm². The length ($L_2$) is 1–5 times the diameter of the mixing volume 60 (for circular cross-sections), typically being in the range from 0.5 mm to 2 mm. In the illustrated embodiment, a pair of gas conduits 54 (FIG. 4B) are shown, as illustrated in FIG. 4B. It would also be possible to utilize only a single inlet jet or to provide three, four or more separate inlets, with four inlets 54' being as illustrated in FIG. 4C. Other configurations will also be usable including a continuous annular aperture, as described in connection with FIG. 6, or combinations of perpendicular jets (to break-up agglomerates) and axially directed jets (to induce fluidization gas flow).

Figure 5:
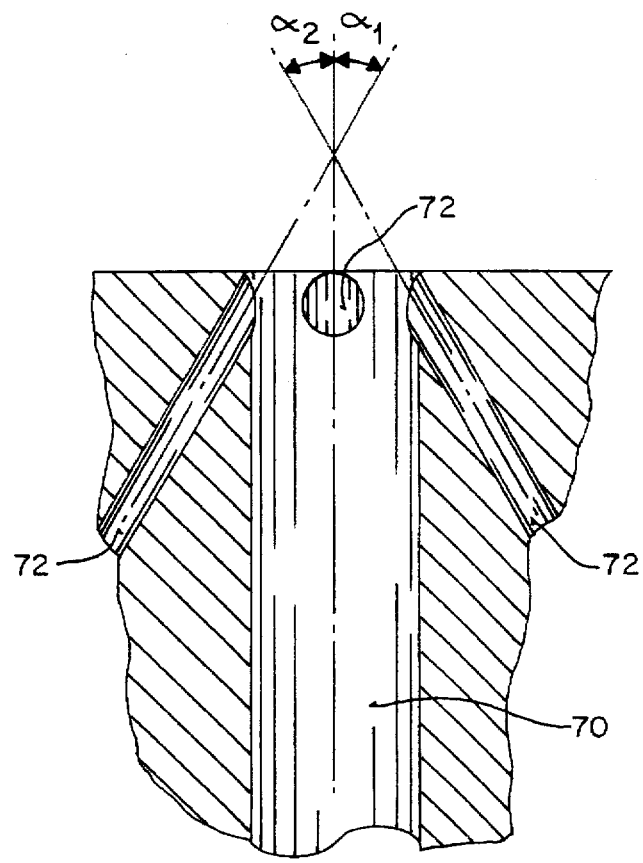
FIG. 5 is a schematic illustration showing the relative sizes and convergence angles of the feed tube lumen and dispersion gas conduits of the present invention.

Referring now to FIG. 5, high pressure gas conduits 72 are arranged around the throat of a feed tube lumen 70 at angles $\alpha_1$, and $\alpha_2$, which will usually but not necessarily be equal. The angles $\alpha$ are important to achieving both adequate mass transfer of powder from the receptacle and adequate "agglomerate break up" as the powder enters the mixing volume immediately downstream from the outlet orifices of the conduits 72. The angles $\alpha$ will be in the range from 12.5° to 65°, preferably being from 25° to 40°.

Figure 6:
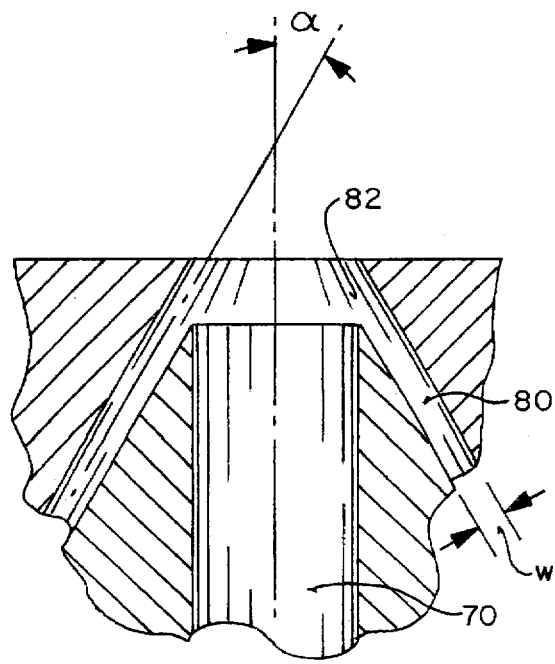
FIG. 6 illustrates a feed tube lumen in combination with a dispersion gas conduit having an annular aperture which defines a conical flow path.

It will be appreciated that the high pressure gas lumens 72, as illustrated in FIG. 5, may be formed as a single conical plenum 80 terminating in an annular aperture 82, as illustrated in FIG. 6. The angle of convergence $\alpha$ will generally be within the range set forth above for $\alpha$ above, and the total area of the annular lumen 82 will generally be within the total area $A_2$ for the high pressure gas lumens also set forth above. Typically, the conical plenum 80 will have a width w in the range from about 0.005 mm to 0.1 mm.

Referring again to FIG. 2, the feed tube assembly 14 operates by coupling the inlet end 16 of the feed tube 40 with an aperture 90 (FIG. 3) formed into lid 92 over a receptacle 12. As illustrated, the inlet end 16 is inserted through the lid 92 and into the receptacle 12, but is will also be feasible to engage the inlet end over the aperture 90, typically utilizing a sealing gasket as illustrated in FIGS. 7–10, below. The aperture 90 will be surrounded by space-apart apertures 94 (illustrated as six) which allow for the entry of fluidizing air as entrained powder is extracted through the inner feed tube 40. The aperture 90 is shown to be centered, but that is not necessary. In a preferred aspect of the present invention, at least a portion (and preferably all) of the fluidizing air will be provided through the annular lumen 44 via a port 96 in the feed tube assembly 14 disposal at the bottom of the interior of the plume chamber 30. Such "recycled" air from the plume chamber 30 passes through an annular plenum 98 from the port 96 into the annular lumen 44. Optionally, a rubber flange or skirt 95 may be provided to prevent loss of fluidizing air from the lumen 44 to the receptacle 12. The recycling of fluidization air from the plume chamber 30 helps contain the plume of dispersed powder within the plume chamber since it limits the amount of air which is displaced and expelled through the mouthpiece 32 or other opening in the chamber.

Introduction of the inlet end 16 of feed tube 40 of the feed tube assembly 14 into the receptacle 12 is advantageous (but not necessary) since it facilitates substantially complete removal of powder (usually at least 80% and preferably at least 90% by weight) from the interior of the receptacle. Such complete removal is further enhanced by the entry of fluidization air through the space-apart apertures 94, which creates an air flow pattern which can sweep powder from all corners of the receptacle into the dispersion lumen 46.

An alternative embodiment of a feed tube assembly 100 is shown in FIGS. 7–9. The feed tube assembly 100 is generally functionally equivalent to the feed tube assembly 14 and can be used in place thereof in the system of FIG. 1. The feed tube 100, however, is particularly suitable for fabrication from molded plastic parts, or from a combination of molded plastic and fabricated metal parts.

Feed tube assembly 100 comprises a casing 102, a gas flow-directing cone 104, a feed tube element 106, an end piece 108, a flexible valve element 110, and an end gasket 112. The feed tube element 106 is received in an open cavity 114 disposed in a lower end of the flow-directing cone 104. The flow passages within feed tube 106 will generally be the same as that described previously for feed tube assembly 14, and feed tube assembly 100 further includes a mixing volume 116 located immediately above the open cavity 114 and an expansion region 118 located above the mixing volume. The dimensions of the mixing volume 116 and expansion region 118 will generally be the same as those described previously in connection with the feed tube assembly 14.

As best seen in FIG. 8, the flow directing cone 104 may include a plurality of air flow channels 120 formed over its exterior surface. Usually, there will be from 1 to 10 channels, having a total cross-sectional area from 5 $mm^2$ to 150 $mm^2$, preferably from 40 $mm^2$ to 100 $mm^2$. The air flow channels 120 are shown in a generally spiral pattern in FIG. 8. The spiral pattern may be preferred since it will impart a vertical flow to replacement air entering the associated plume chamber as the patient inhales. The airflow channels 120, however, could also have a generally straight configuration which would impart a conically expanding, but not spiral, flow pattern to the replacement air. It would also be possible to employ air flow channels which are straight and parallel to each other to impart a general axial replacement airflow pattern into the plume chamber. It will also be possible to employ a single annular opening by using pins of other non-dividing elements for supporting the flow-direction cone, where the cone may have a continuous surface without discrete channels.

The airflow channels 120 are enclosed at their outward extremities by the inner surface 122 (FIG. 9) of the casing 102. The air flow channels thus extend from a lower end 124 to an upper end 126, providing flow paths for replacement or "chase" air into a plume chamber, as described in more detail below. The flow paths provided by air channels 120 will also provide for recycling of air in the reverse direction from the plume chamber to an associated powder receptacle when the powder is being fluidized. This function will be described in more detail below.

The end piece 108 includes a plurality of air flow apertures 126 located around a central opening 128. The flexible valve 110 lies over the air flow apertures 126 and is secured between the lower end of casing 102 and the upper surface of the end piece, as best seen in FIG. 9. The flexible valve element 110 generally acts as a one-way valve, permitting entry of air from the outside of the feed tube assembly 100 into the region formed between the lower end of casing 102 and the end piece 108.

High pressure air will be able to enter the open cavity 114 formed at the outlet end of feed tube element 106 through an inlet port 130 formed in the casing 102 (FIG. 7). For simplicity, the flow path from port 130 to the cavity 114 is not shown in FIG. 9. Supply of high pressure gas to the cavity 114 acts to induce the flow of fluidization air through the central lumen of the feed tube element 106 in a manner completely analogous to that described previously for feed tube assembly 14.

Figure 9:
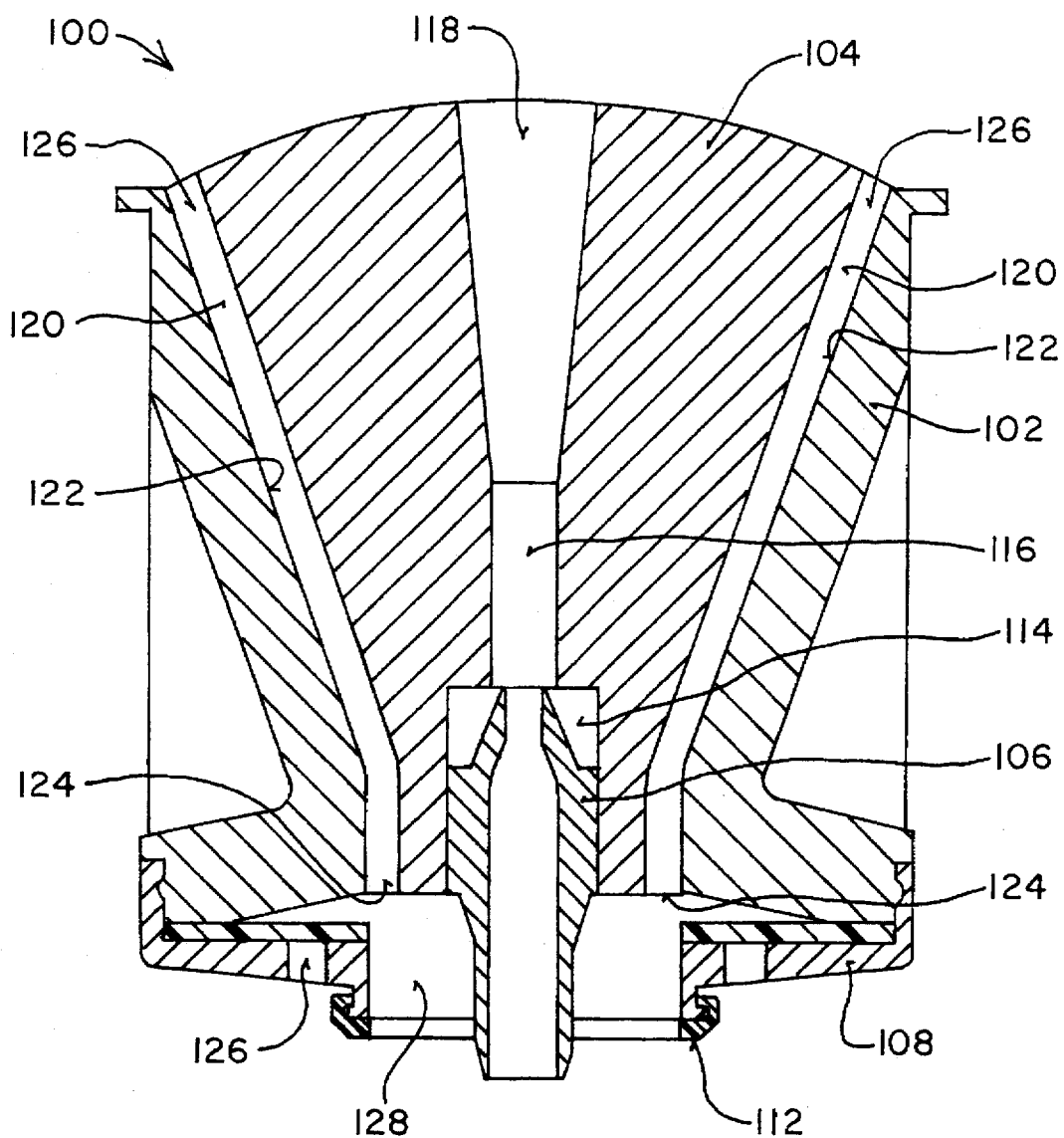
FIG. 9 is a cross-sectional view of the feed tube assembly of FIG. 7
Figure 10:
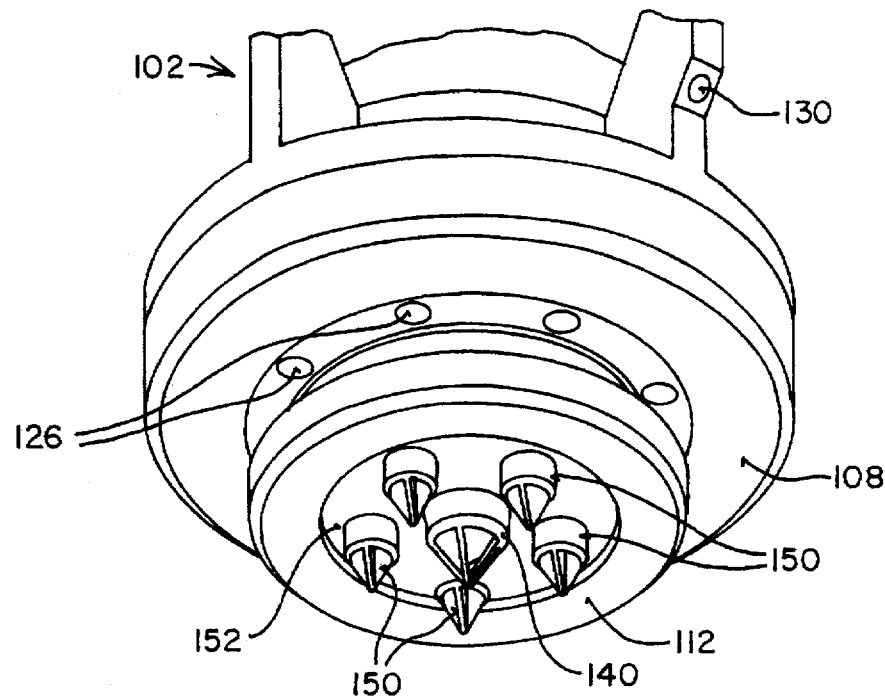
FIG. 10 illustrates a third alternative feed tube assembly, similar to that of FIG. 7–9, but further including self-penetrating elements which permits entry of the feed tube and fluidization air tubes into a powdered medicament receptacle.
Figures 11A, 11B:
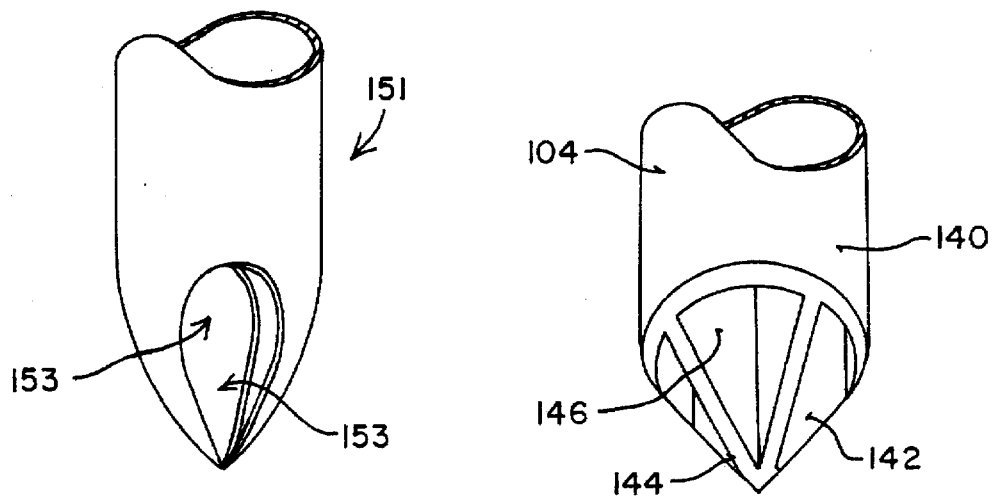
FIG. 11A is an enlarged, detailed view of the self-penetrating elements of FIG. 10.
FIG. 11B is an enlarged view of an alternative construction of a self-penetrating element.

Referring now to FIGS. 10 and 11A, a modification of the feed tube assembly 100 which permits direct penetration of a medicament receptacle lid is shown. For convenience, all elements which correspond to those shown in FIG. 7–9 will be numbered identically. A feed tube penetrating element 140 is disposed at the lower end of the feed tube 106. As shown in detail in FIG. 11, the penetrating element 140 includes a pair of crossing internal walls 142 which terminate in a pointed blade structure 144. The blade structure 144 leaves four separate flow passages 146 arranged in quadrants within the feed tube 104. The flow passages 146 may optionally stop beyond the attachment point of the blade structure 144 to the inside wall of the host tube.

A plurality of similar penetrating structures 150 are provided for both piercing the receptacle lid and simultaneously providing fluidization air inlet paths. The penetrating structures 150 may be provided in a carrier plate 152 or similar supporting structure. The penetrating structures 150 will have a similar conical blade structure to that described previously for the feed tube penetrating structure 140. Thus, the structure of FIG. 10 can provide for both the feed tube penetration and the peripherally arranged fluidization air penetrations in the penetrable lid of a medicament receptacle in a single motion where the lid is drawn against the gasket 112 of the feed tube assembly 100.

FIG. 11B illustrates an alternative penetrating structure 151 formed by machining the end of a tube along two converging planes. The resulting pointed elements are then pressed together to form the structure having openings 153. The penetrating element 151 is advantageous since it peels back the lid as it is penetrated, leaving the openings 153 clear to receive powder. The penetrating structure 151 could be fabricated from molded plastic as well as machined metal.

Figure 7:
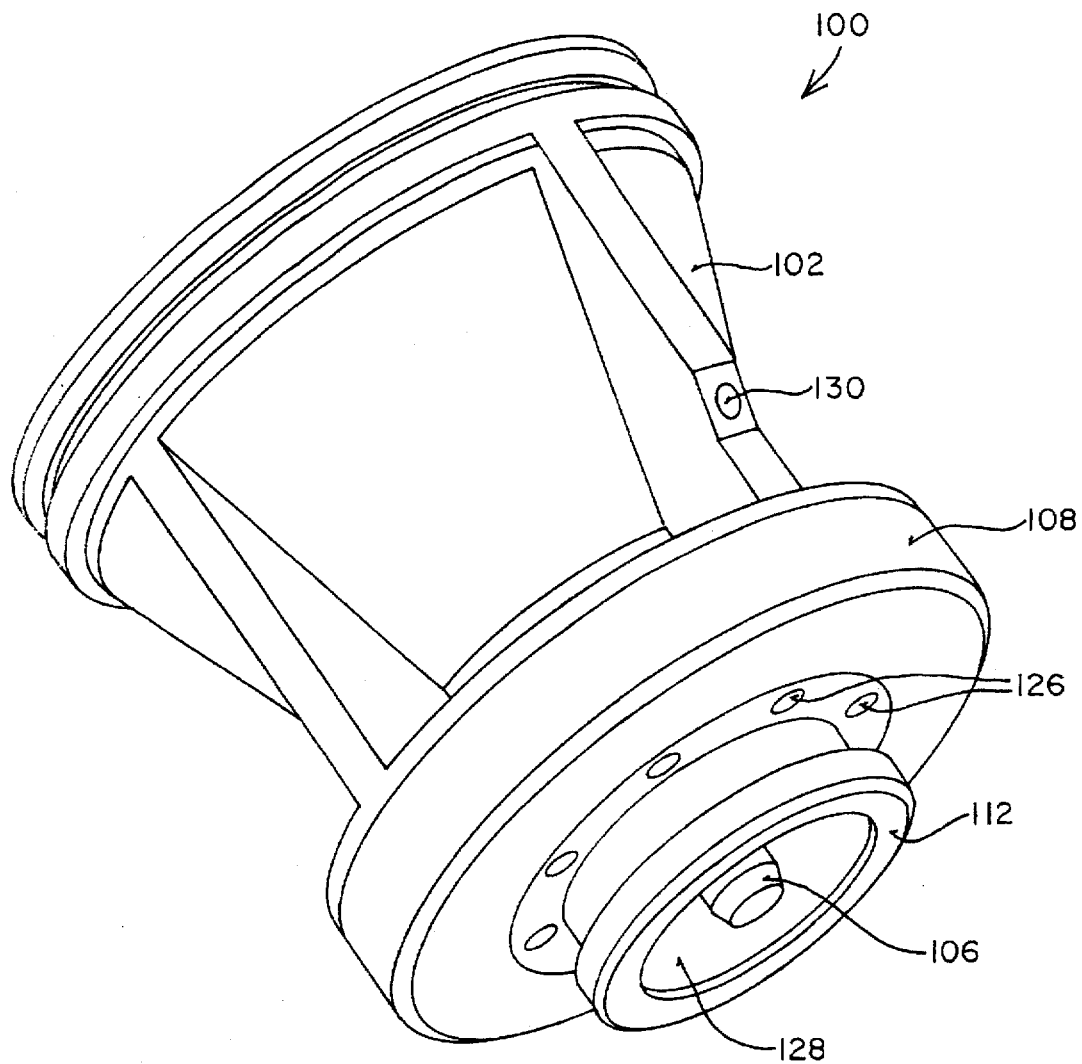
FIG. 7 is a perspective view of an alternative feed tube assembly constructed in accordance with the principles of the present invention.
Figure 8:
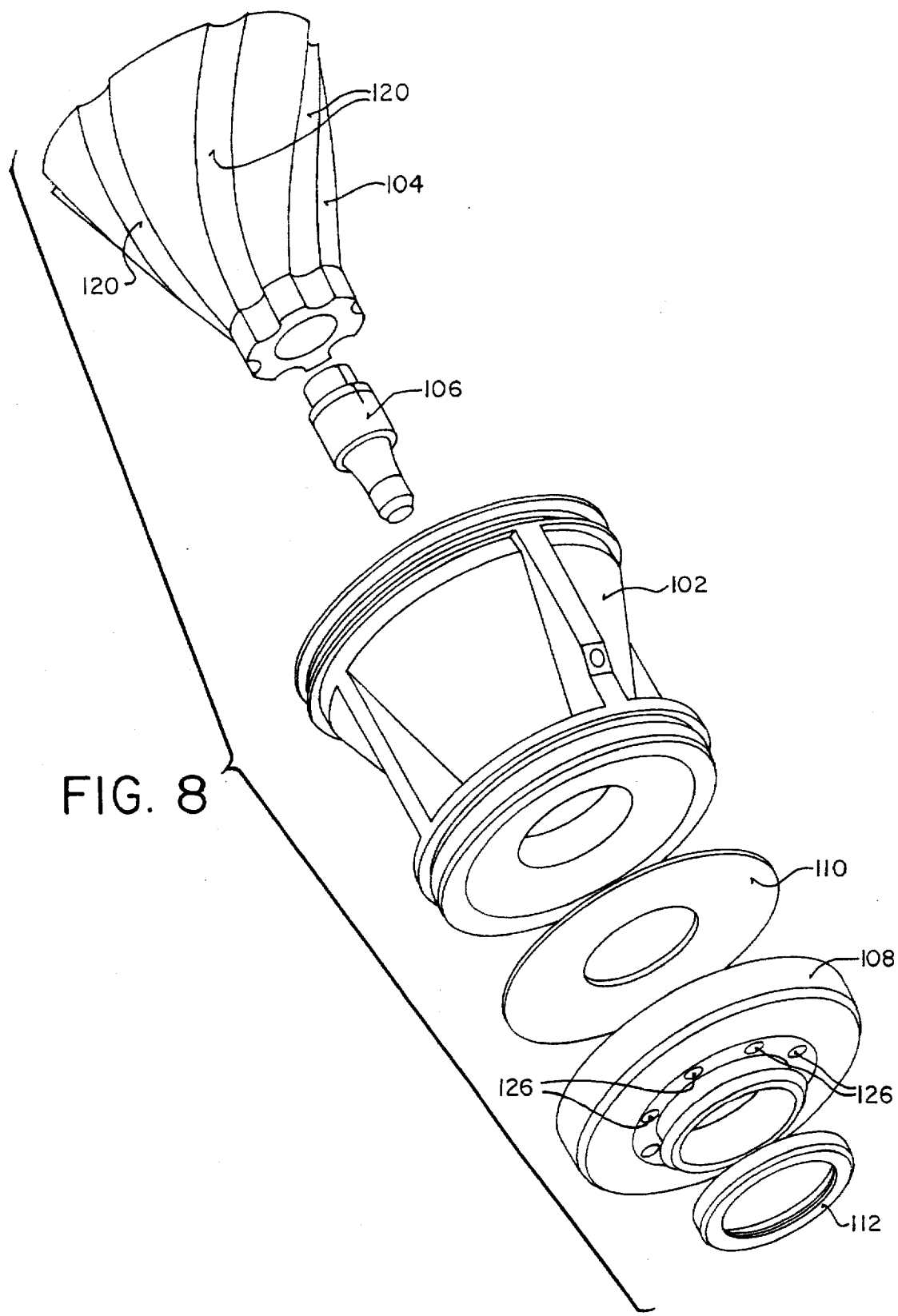
FIG. 8 is an exploded view of the feed tube assembly of FIG. 7.
Figure 12A:
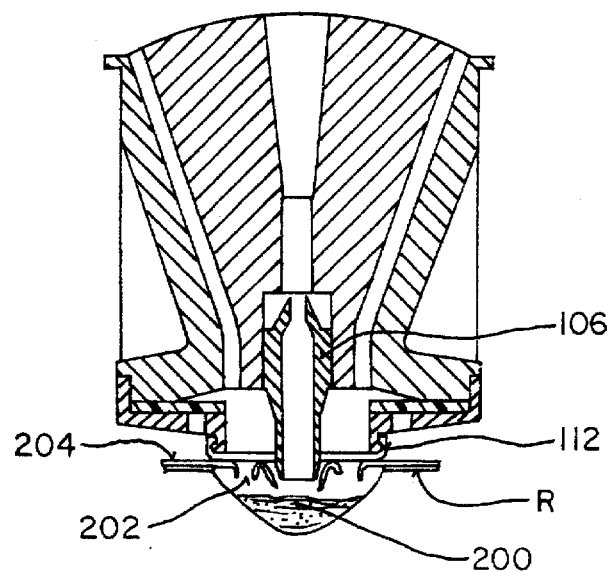
FIGS. 12A–12C illustrate use of the feed tube assembly of FIGS. 7–9 in dispersing a powdered medicament from a single unit dosage receptacle.
Figure 12B:
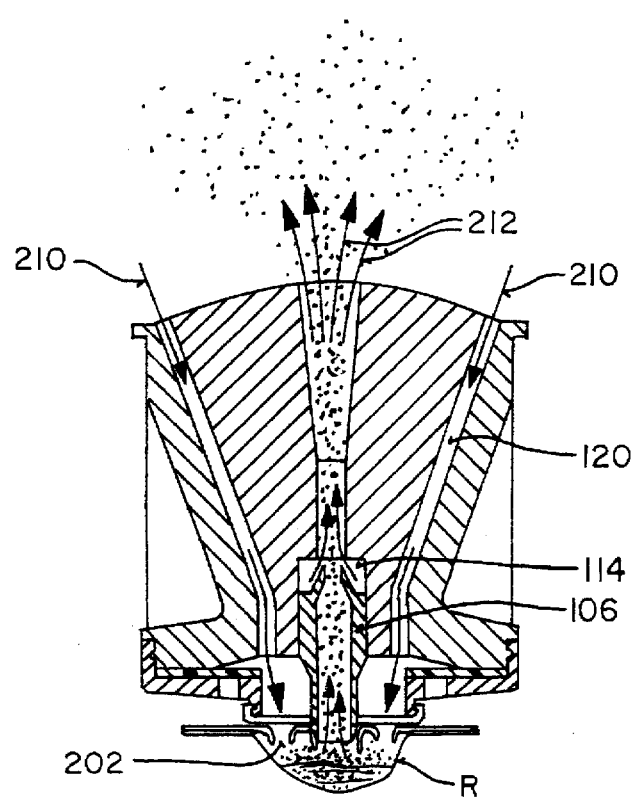
Figure 12C:
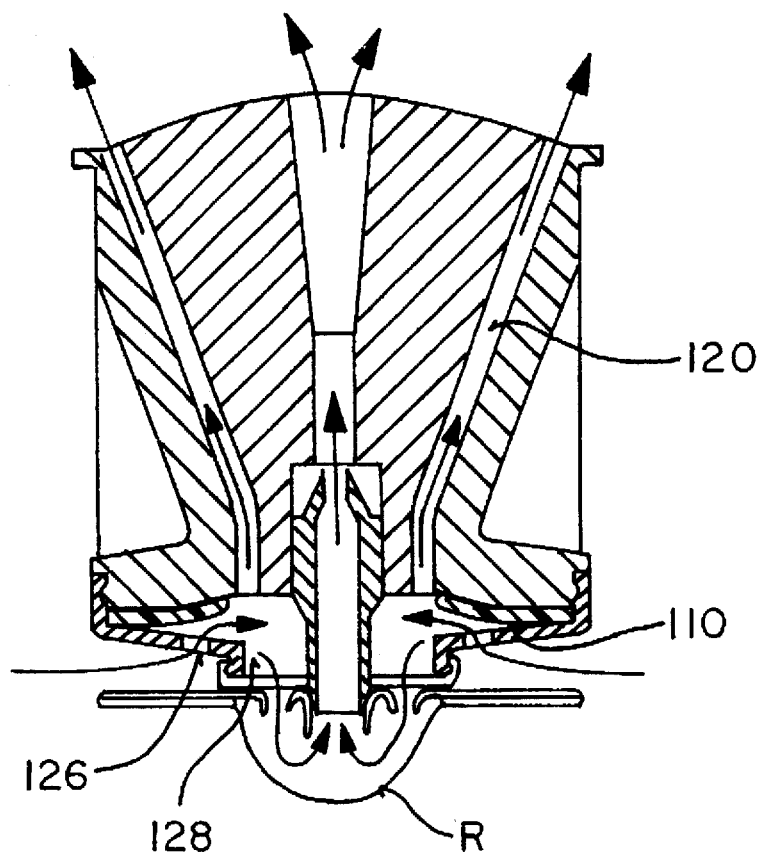

Referring now to FIGS. 12A–12C, use of the feed tube assembly 100 of FIGS. 7–9 will be described in more detail. Initially, a medicament receptacle R having preformed feed tube and fluidization air penetrations 200 and 202 is engaged against the gasket 112, as illustrated in FIG. 12A. Gasket 112 provides a seal against penetrable lid 204 of the receptacle R. The inlet end of feed tube 106 is shown to penetrate the lid 104, but it will be appreciated that such penetration is not essential since a seal will be provided by the gasket 112. Penetration may be desirable, however, since the lid flaps which surround the penetration 200 will be held open.

After the receptacle R is in place, a burst of high pressure air is introduced into the open cavity 114, as shown in FIG. 12B. The high pressure air flows past outlet end of the feed tube 106, inducing a flow of fluidization air through the receptacle R. In particular, fluidization air is drawn through the air flow channels 120 from the overlying plume chamber (not illustrated), as shown by arrows 210. The air drawn in through the air flow channels 120 enters the receptacle through penetrations 202, thus fluidizing the powder and drawing the powder out through the feed tube 106. The air flow through the feed tube thus entrains the powder and combines the powder with high pressure gas flow at the outlet end of the feed tube. The combined powder, fluidization air, and high pressure dispersion gas is then introduced into the plume chamber, as shown by arrows 212.

After the powder has been dispersed, patient will inhale from the plume chamber which will cause a reverse flow of air through the air flow channels 120, as illustrated in FIG. 12C, ambient air will enter the central opening 128 through apertures 126 as the flexible valve element 110 opens. The air which enters through apertures 126 will primarily pass through the air flow channels 120. A portion, however, may pass back into the receptacle R and upward through the feed tube into the plume chamber. Such flow through the receptacle will further empty the receptacle of any powder which may remain.

Figure 13:
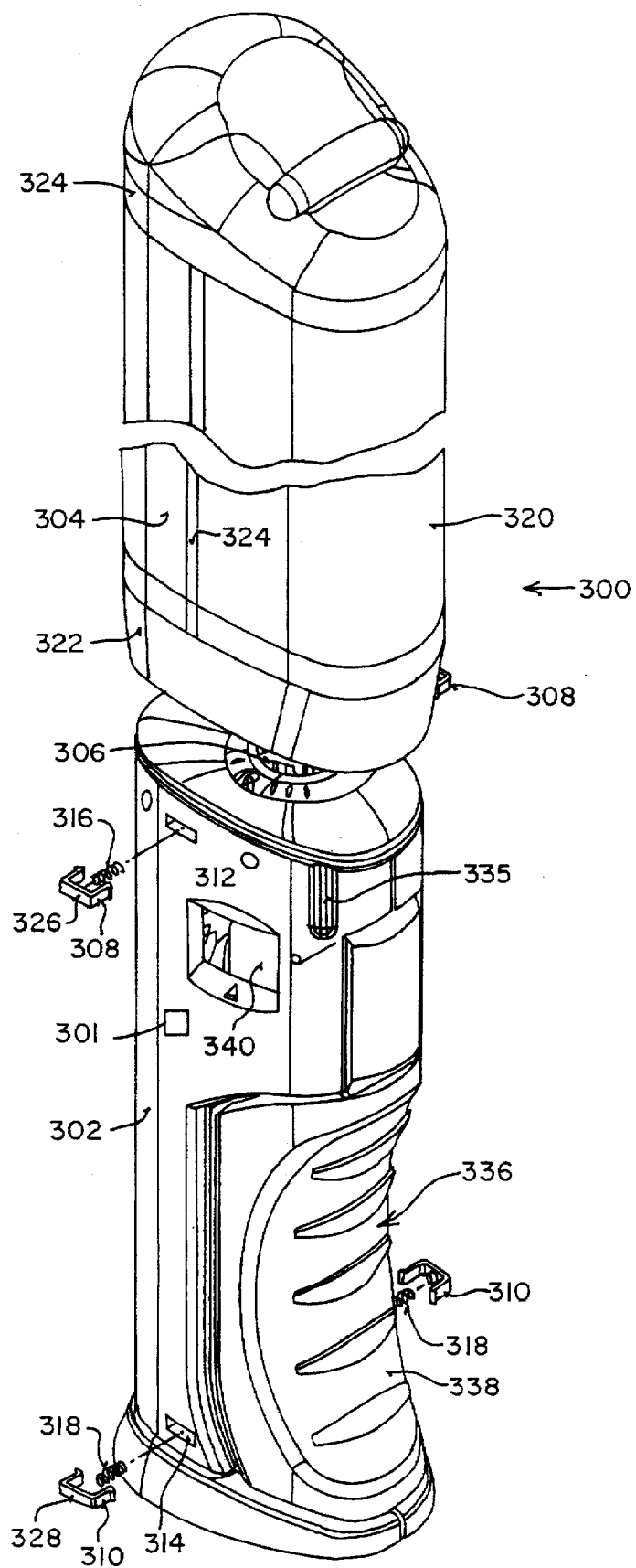
FIG. 13 is a perspective view of a particularly preferable apparatus for aerosolizing a powdered medicament according to the present invention.
Figures 20, 20A:
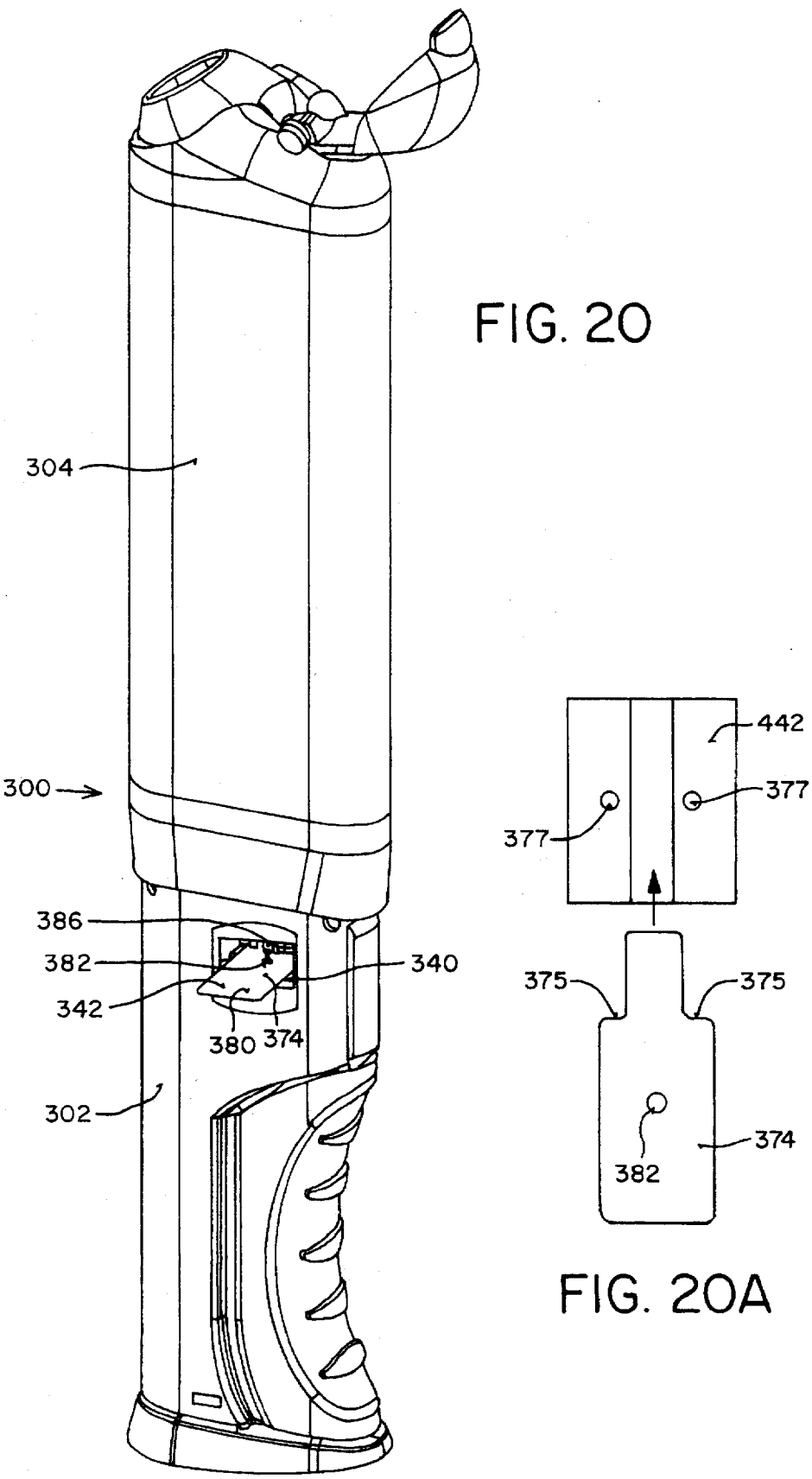
FIG. 20 is a perspective view of the apparatus of FIG. 13 showing introduction of a receptacle having the powdered medicament into the apparatus.
FIG. 20A is a top view of the receptacle being placed onto a carrier of the apparatus of FIG. 13.

Referring to FIG. 13, a particularly preferable embodiment of an aerosolizing apparatus 300 will be described. The apparatus 300 includes a housing 302 and a capture chamber 304 that is slidable over the housing 302. Removably held within the housing 302 is a TRANSJECTOR™ multi-flow ejector assembly 306. The TRANSJECTOR™ multi-flow ejector assembly 306 is similar to the feed tube assembly 100 as shown in FIGS. 7–9 and is employed to introduce aerosolized medicament into the capture chamber 304 as described in greater detail hereinafter. The apparatus 300 further includes a handle assembly 336 having a handle 338 that in combination with the TRANSJECTOR™ multi-flow ejector assembly 306 is employed to aerosolize the medicament and will be described in greater detail hereinafter. The housing 302 further includes an aperture 340 for receiving a receptacle 342 (see FIG. 20) having the powdered medicament.

Figure 14:
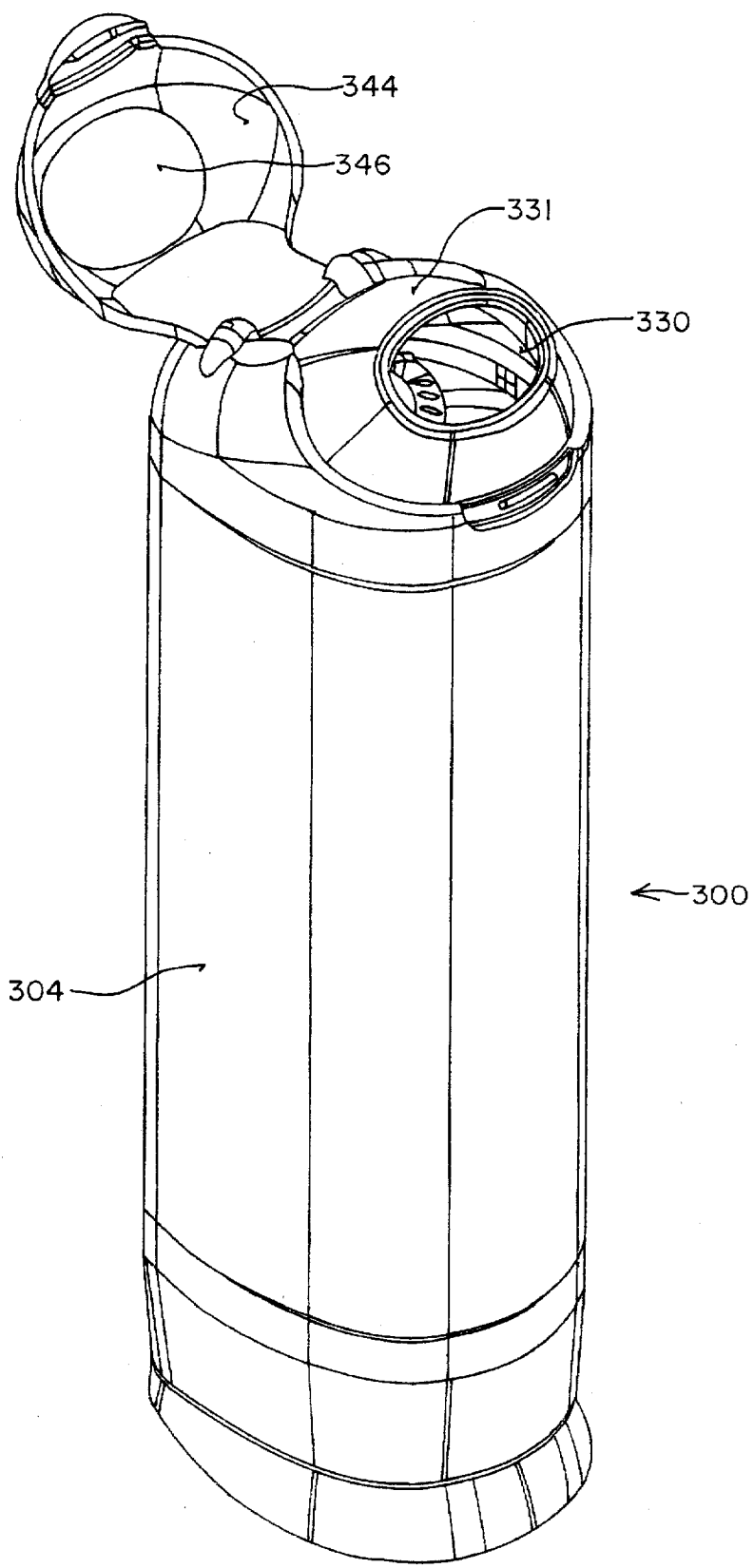
FIG. 14 is a perspective view of the apparatus of FIG. 13 rotated 180 degrees and showing a capture chamber in a collapsed configuration and a mouthpiece on the chamber.
Figure 15:
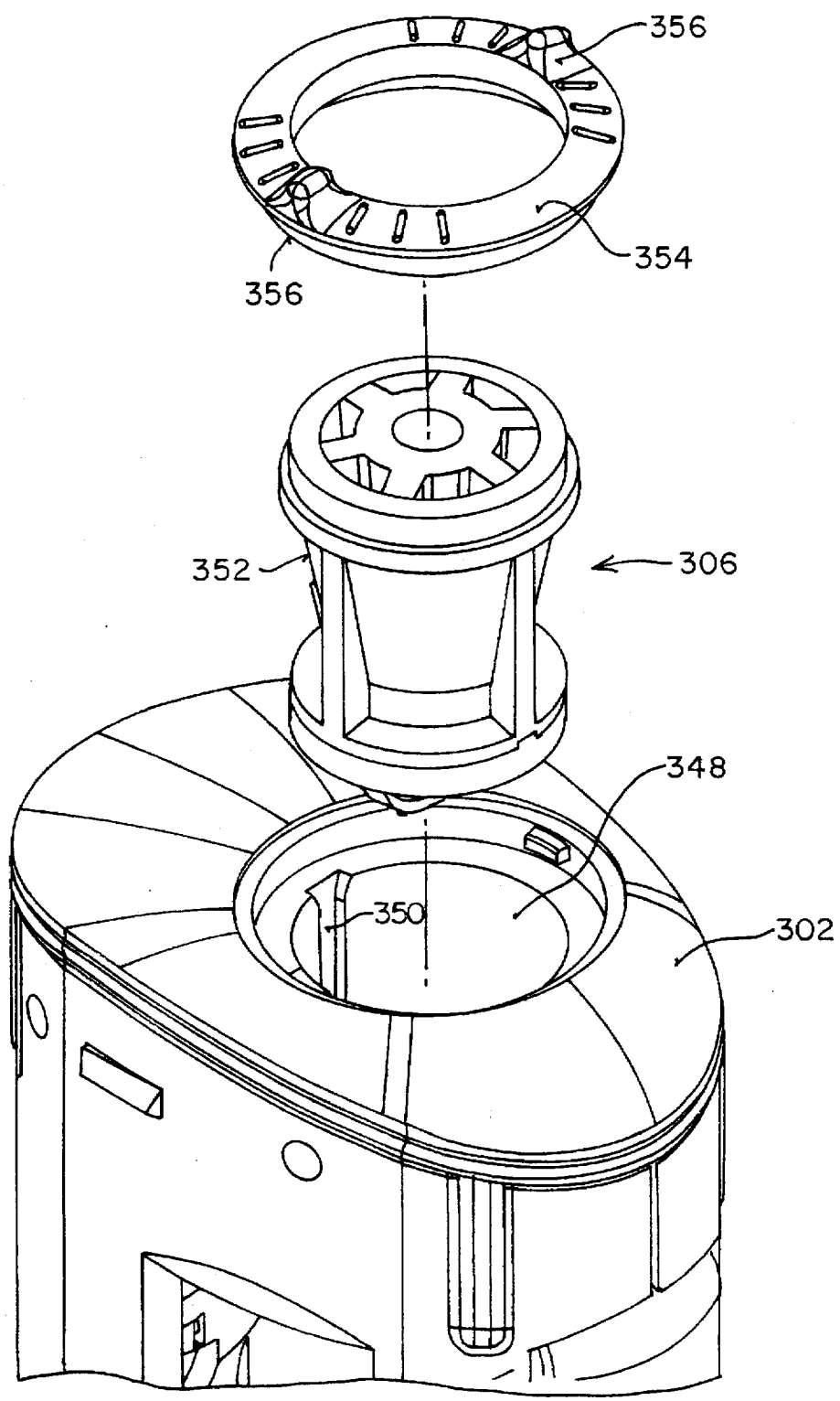
FIG. 15 is an exploded perspective view of the apparatus of FIG. 13 showing a TRANSJECTOR™ multi-flow ejector assembly for aerosolizing the powdered medicament according to the present invention.
Figure 16:
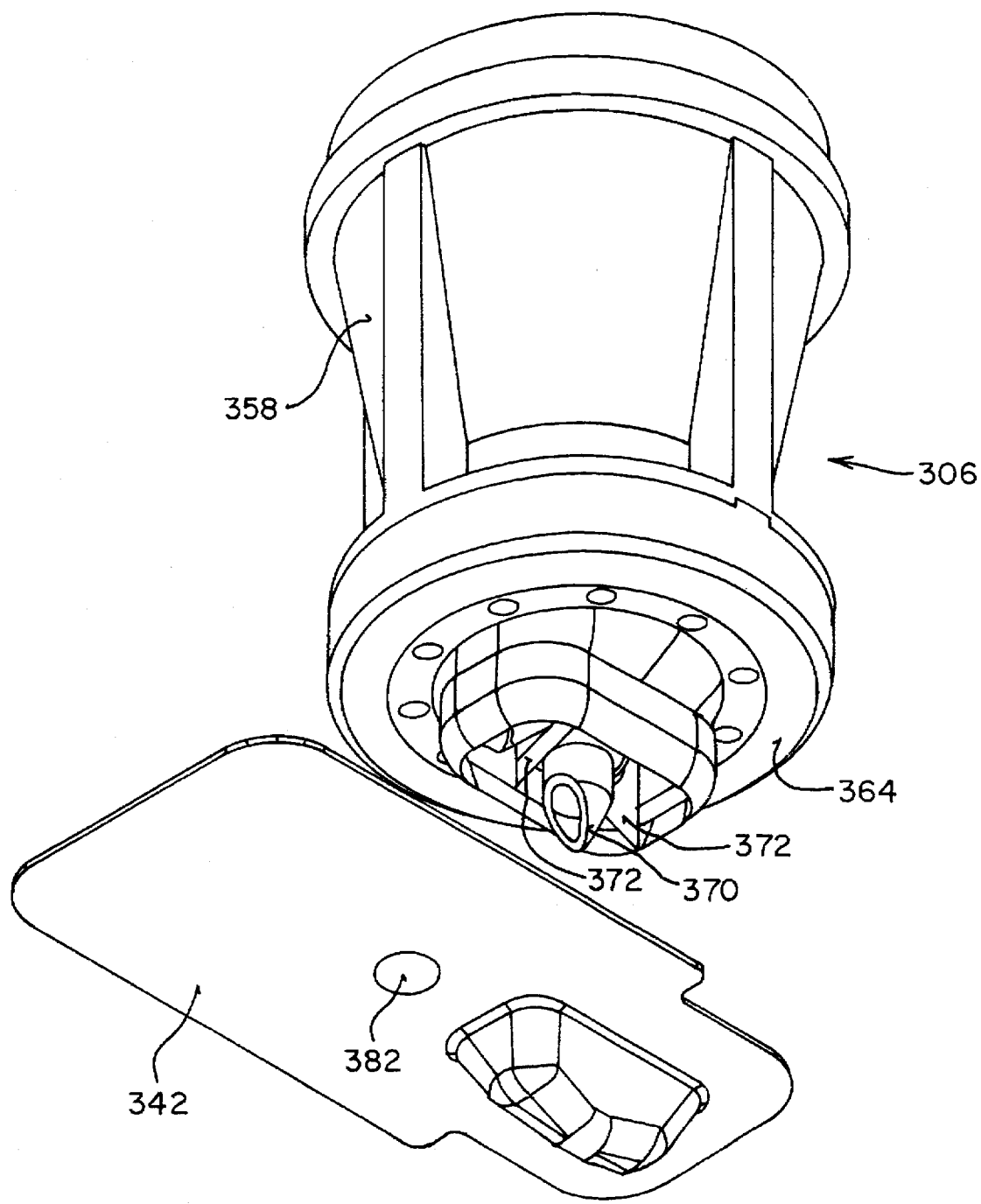
FIG. 16 illustrates the TRANSJECTOR™ multi-flow ejector assembly of FIG. 15 positioned over an exemplary receptacle for holding the powdered medicament according to the present invention.
Figure 17:
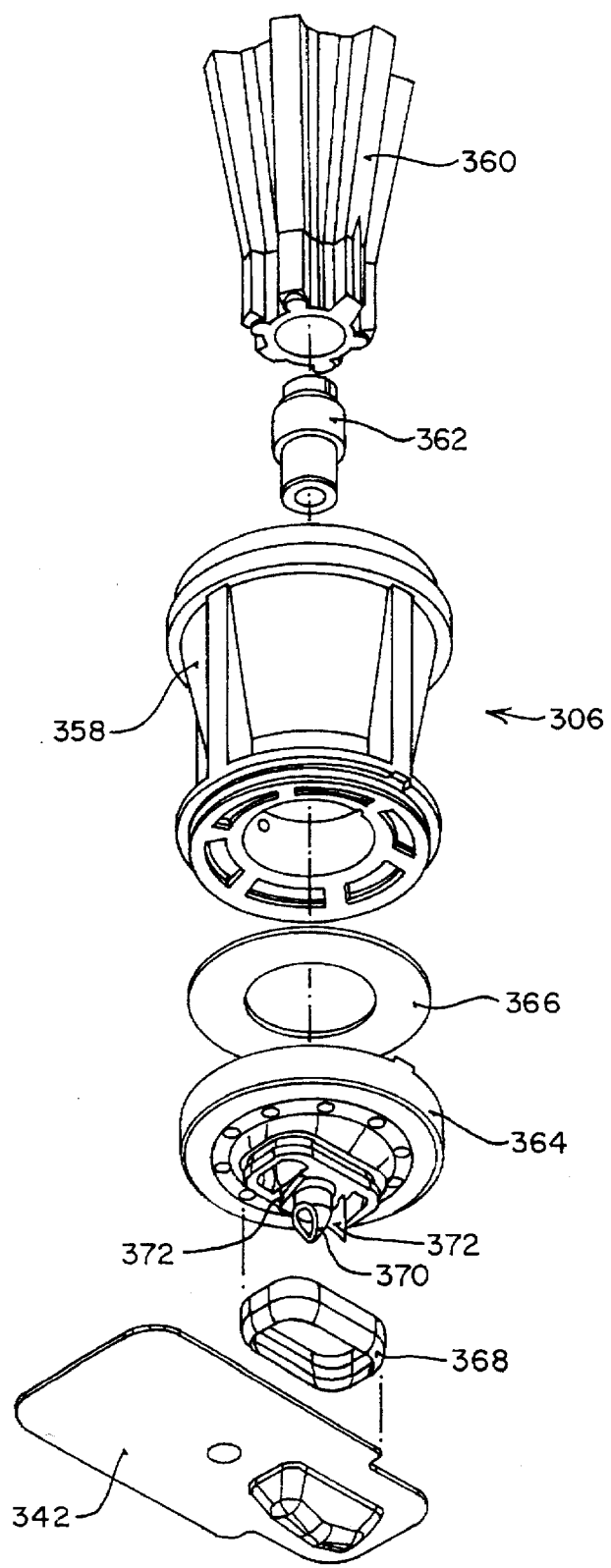
FIG. 17 is an exploded view of the TRANSJECTOR™ multi-flow ejector assembly of FIG. 16.
Figure 18:
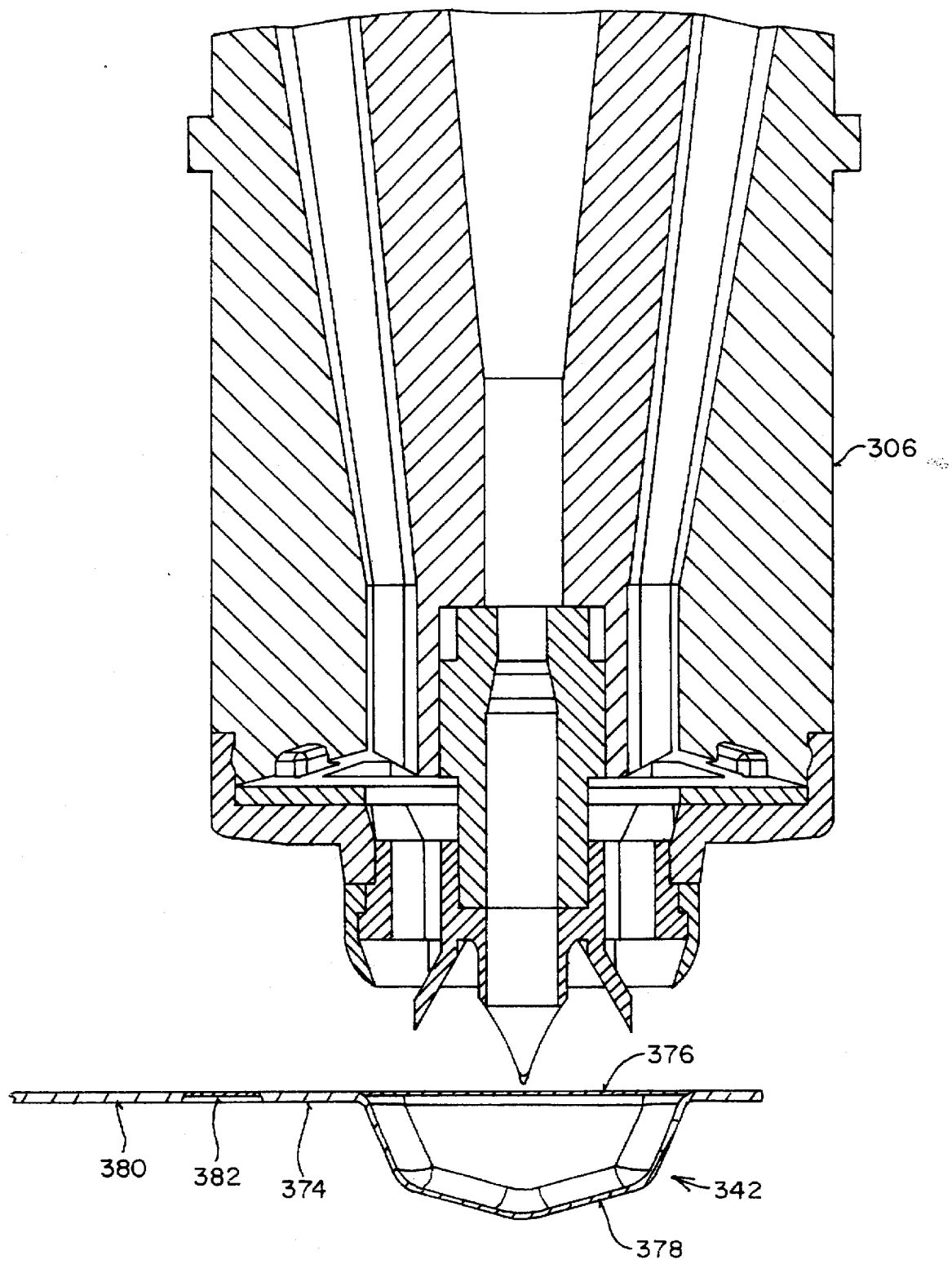
FIG. 18 is a cross-sectional view of the TRANSJECTOR™ multi-flow ejector assembly and receptacle of FIG. 16.
Figure 19:
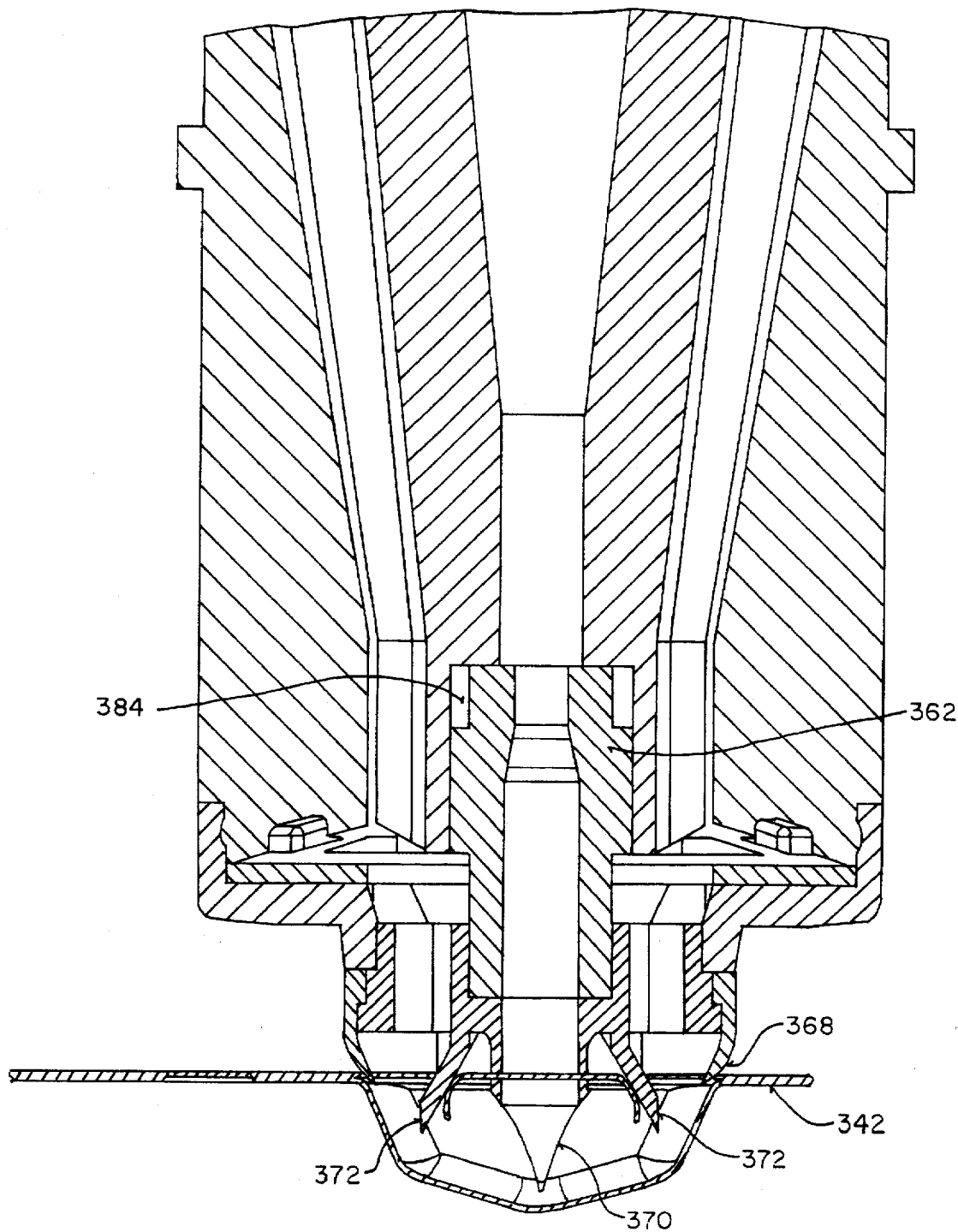
FIG. 19 illustrates penetration of the TRANSJECTOR™ multi-flow ejector assembly of FIG. 19 into the receptacle.

The capture chamber 304 is sized to be slidably received over the housing 302 so that the capture chamber 304 may be removed from the housing 302 for cleaning and also so that chamber 304 can be translated between a deployed position (see FIG. 20) and a retracted position (see FIG. 14). In the deployed position, the capture chamber 304 forms an enclosure for receiving aerosolized medicament introduced by the TRANSJECTOR™ multi-flow ejector assembly 306 so that it may be inhaled by a patient. Following inhalation, the capture chamber 304 can be slid over the housing 302 to the retracted position for storing. To hold the capture chamber 304 in the retracted and the deployed positions, two pairs of detent pins 308 and 310 are provided. The detent pins 308, 310 are received into slots 312 and 314 in the housing 302. Springs 316 and 318 are preferably provided to outwardly bias the detent pins 308, 310. The capture chamber 304 includes a chamber body 320 having a bottom portion 322 and a top portion 324. Included in the bottom portion 322 are a pair of grooves (not shown) for engaging the detent pins 308, 310. The detent pins 308 are received in the grooves when the capture chamber 304 is in the deployed position, and the detent pins 310 are received into the grooves when the capture chamber 304 is in the retracted position. The detent pins 308 and 310 each include a V-shaped portion 326 and 328 for engaging the grooves in the bottom portion 322 of the capture chamber 304. The particular angle and orientation of the V-shaped portions 326 and 328 can be varied to increase or decrease the amount of force required to deploy or retract the capture chamber 304. The mating grooves on the chamber 204 may also be provided with different angles to assist in achieving this effect. Usually, the detent pins 310 will be configured so that it is easier to translate the chamber 304 downward toward the bottom of the housing 302 than to translate the chamber 304 upward toward the top of the housing 302. In this manner, the chamber 304 may be placed in the retracted or storage position with a relatively small force, while a relatively greater force will be required to retrieve the chamber 304 from the storage position. In this way, the chamber 304 will be configured to not inadvertently slide open during non-use. In a similar manner, the detent pins 308 will usually be configured so that a greater force is required to altogether remove the chamber 304 from the housing 302 than to slide the chamber 304 down over the housing toward the detent pins 308. In this way, inadvertent removal of the chamber 304 will be prevented when sliding the chamber 304 to the deployed position.

Figure 21:
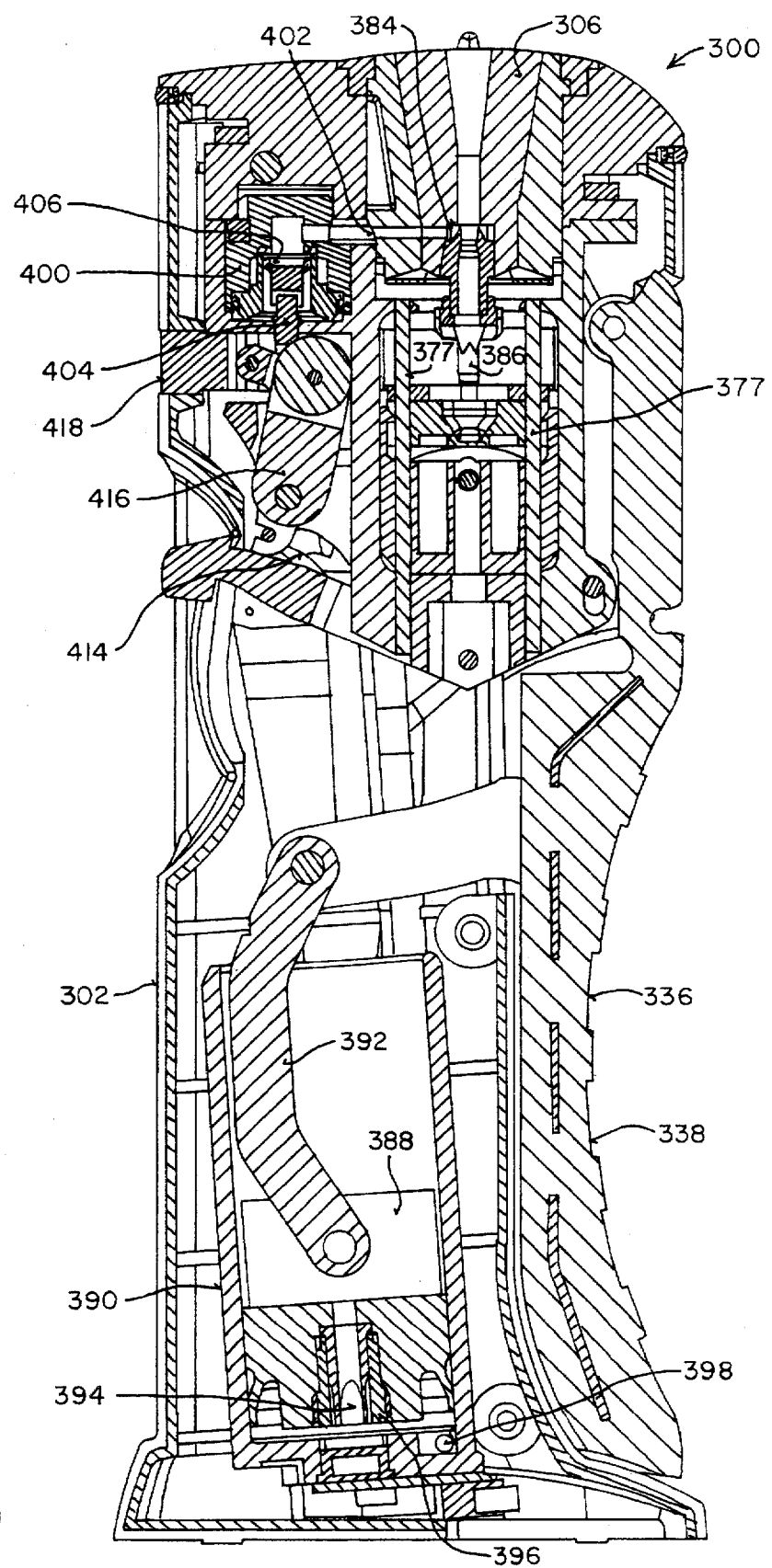
FIG. 21 is a cross-sectional side view of the apparatus of FIG. 13.

The capture chamber 304 is preferably asymmetrical in cross-sectional geometry so that the capture chamber 304 may be repeatedly placed over the housing 302 at a known orientation. This is particularly advantageous in insuring that an inhalation port 330 of a mouthpiece 331 (see FIG. 14) is properly positioned relative to a fire button 418 (see FIG. 21) that is employed to introduce the powdered medicament into the capture chamber 304. In another aspect, the chamber body 320 will preferably include at least one elongate ridge 324 extending longitudinally along the length of the interior of the chamber body 320. The ridge 334 is provided to contact the housing 302 and to keep the remainder of the chamber body 320 spaced-apart from the housing 302 when the capture chamber 304 is translated to the retracted position. Often, residual powder will remain on the interior walls of the chamber body 320 after use. As the chamber body 320 is slid over the housing 302 to retract the capture chamber 304, the ridge 334 contacts the housing 302 to limit the amount of residual powder that is scraped from the chamber body 320 by the housing 302. Extensive scraping of the accumulated powder from the walls of the chamber body 320 is undesirable in that the scraped powder may become agglomerized and may interfere with the subsequent operation of the apparatus 320. In a further aspect, a raised portion 335 is provided on the housing 302 to insure a proper fit between the bottom portion 322 and the housing 302.

The chamber body 320 is preferably constructed of a transparent material and will usually be constructed of plastic. Optionally, the plastic may be an inherently conductive polymer such as that described in U.S. Pat. Nos. 5,342,889, 5,348995, and 4,719263, the disclosure of which is herein incorporated by reference, to limit the amount of electric charge built up on the walls of the chamber body 320 during use.

Referring to FIG. 14, the capture chamber 304 is shown in the retracted position and will be used to describe operation of the inhalation port 330 in greater detail. The capture chamber 304 includes a cover 344 that may be closed over the inhalation port 330. The cover 344 is employed to prevent external dust or particulate from entering into the interior of the capture chamber 304 during storage and also to hold the aerosolized medicament introduced by the TRANSJECTOR™ multi-flow ejector assembly 306 within the chamber 304 until ready for inhalation. Optionally, the cover 344 may include seal 346 which is received over the inhalation port 330 when the cover 344 is closed. When introducing the aerosolized medicament, the pressure within the capture chamber 304 is increased. The seal 346 serves as a bleed valve to allow some of the pressurized gas within the chamber 304 to spontaneously escape. Reducing the chamber pressure in this manner is advantageous in preventing a "puff" of medicament from escaping when the cover 344 is lifted for inhalation.

The capture chamber 304 will preferably define an enclosed volume of about 50 ml to 750 ml, and more preferably at about 100 ml to 250 ml. When the aerosolized medicament is introduced into the chamber 304, the pressure inside will increase over ambient in proportion to the amount of net gas exhausted into the chamber and the volume of the chamber as dictated by Boyles' law where $P_1V_1=P_2V_2$, T=constant at equilibrium. For example, 8 ml of gas introduced into a 210 ml chamber will amount to a pressure rise of about 0.6 psi. Thus, it is desirable for the seal 346 to allow approximately 8 ml of gas to escape to drop the pressure by 0.6 psi. The seal 346 is preferably constructed of silicone, urethane or similar flexible elastomers, although a similar functioning valve could be achieved with a spring loaded rigid valve element such as a thin mylar or metal petal or plate.

Referring to FIG. 15, placement of the TRANSJECTOR™ multi-flow ejector assembly 306 into the housing 302 will be described in greater detail. The housing 302 includes a cylindrical opening 348 that is sized to receive the TRANSJECTOR™ multi-flow ejector assembly 306. The opening 348 includes a keyed slot 350 for receiving a keyed portion 352 of the assembly 306. The keyed slot 350 is provided so that the TRANSJECTOR™ multi-flow ejector assembly 306 may be repeatedly placed in a known orientation when the TRANSJECTOR™ multi-flow ejector assembly 306 is inserted into the opening 348. A locking nut 354 is provided to secure the TRANSJECTOR™ multi-flow ejector assembly 306 into the opening 348. The locking nut 354 includes a pair of tabs 356 to allow for easier rotation of the nut 354 when securing or unlocking the nut 354. To remove the TRANSJECTOR™ multi-flow ejector assembly 306, the nut 354 is unscrewed and removed, and the TRANSJECTOR™ multi-flow ejector assembly 306 is lifted from the housing 302. Alternatively, the nut 354 may be configured to snap fit into the opening 348 to hold the TRANSJECTOR™ multi-flow ejector assembly 306 in place.

Referring to FIGS. 16 and 17, construction of the TRANSJECTOR™ multi-flow ejector assembly 306 along with the receptacle 342 will be described in greater detail. As best shown in FIG. 17, the TRANSJECTOR™ multi-flow ejector assembly 306 includes a casing 358, a gas flow directing cone 360, a feed tube element 362, an end piece 364, a flexible valve element 366, and an end gasket 368. The TRANSJECTOR™ multi-flow ejector assembly 306 operates substantially identically to the feed tube assembly 100 as shown in FIGS. 7–9 in extracting and aerosolizing the powdered medicament in the receptacle. The TRANSJECTOR™ multi-flow ejector assembly 306 differs from the feed tube assembly 100 in that the TRANSJECTOR™ multi-flow ejector assembly 306 includes an alternative penetrating element 370 and a pair of penetrating structures 372. The penetrating element 370 is disposed at the lower end of the feed tube 362 and is employed to extract powder from the receptacle 342 as previously described in connection with the feed tube assembly 100 when the penetrating element 370 is introduced into the receptacle 342. The penetrating structures 372 are provided for both piercing the receptacle lid and simultaneously providing fluidization air inlet paths. A particular advantage of the penetrating structures 372 is that they are easy to manufacture, thereby reducing the overall cost of the TRANSJECTOR™ multi-flow ejector assembly 306. As best shown in FIGS. 21, 23 and 24, the penetrating structures 372 may optionally be provided with a plurality of points rather than a single point to facilitate penetration into the receptacle lid.

As best shown in FIGS. 18 and 19, the receptacle 342 includes a receptacle body 374 having a penetrable lid 376 covering an enclosure 378 and a tab 380. Within the tab 380 is a hole 382 for aligning the receptacle 342 with the TRANSJECTOR™ multi-flow ejector assembly 306 as described in greater detail hereinafter.

To penetrate the lid 376, the receptacle 342 is lifted (or the TRANSJECTOR™ multi-flow ejector 306 is lowered) until the penetrating element 370 and the penetrating structures 372 pierce the lid 376 as shown in FIG. 19. The penetrating structures 372 are angled relative to the penetrating element 370 and operate similar to can openers to peel back a portion of the lid 376 and form the air inlet paths. Once the receptacle 342 is in place, a burst of high pressure air is introduced into an open cavity 384 which flows past the outlet end of the feed tube 362 to draw the powdered medicament within the receptacle 342 through the TRANSJECTOR™ multi-flow ejector assembly 306 in a manner similar to the feed tube assembly 100 described in FIGS. 12–12C. When the penetrating element 370 and the penetrating structures 372 pierce the lid 376, the end gasket 368 contacts the receptacle body 374 and forms a seal against the receptacle 342.

Referring to FIGS. 20 and 20A, placement of the receptacle 342 into the aperture 340 will be described in greater detail. The receptacle 342 is delivered into the aperture 340 by grasping the tab 380 and inserting the receptacle body 374 into the aperture 340 until stop shoulders 375 on the receptacle body 374 engages guide pins 377 (see also FIG. 21) on which a carrier 442 (see also FIG. 22) rides and prevents further translation. At this point, the hole 382 is generally aligned with a pin 386. The receptacle 342 is then lifted within the aperture 340 until the hole 382 is received over the pin 386 which guides and aligns the receptacle 342 until engaging the end gasket 368 (see FIG. 19). At all times, the tab 380 remains outside the housing 302. In this way, premature closure of the capture chamber 304 is prevented since the tab 380 will prevent retraction of the capture chamber 304. The tab 380 thus ensures that the capture chamber 304 will always be in the deployed position when the receptacle 342 is loaded into the apparatus 300. Thus, the capture chamber 304 must always be in the deployed position for the receptacle 342 to be loaded into the apparatus 300. Optionally, the pin 386 may be keyed to fit only a specific hole configuration in the receptacle 342. In this manner, the apparatus may be configured to receive only specific receptacles having a given medicament. Alternatively, a plurality of pins and corresponding holes in the receptacle may be provided to key the apparatus 300.

Referring to FIGS. 21–27, operation of the apparatus 300 to produce an aerosolized medicament will be described. As shown in FIG. 21, the handle 338 on the handle assembly 336 is operably connected to a piston 388 that in turn is translatably held within a cylinder 390. A linkage 392 is provided to connect the piston 388 to the handle 338. As best shown in FIGS. 25 and 26, as the handle 338 is moved radially outward away from the housing 302, the linkage 392 is pulled from the cylinder 390 to lift the piston 388. When the handle 388 is fully extended (FIG. 25), the piston 388 is in a retracted position. As the handle 338 is translated back toward the housing 302, the piston 388 is translated within the cylinder 390 to pressurize the gas within the cylinder 390. As best shown in FIG. 21, the cylinder includes a one-way valve 394 that is held within a retainer 396. The one-way valve 394 is preferably a "duck bill" type valve which allows air into the cylinder 390 as the piston 388 is translated to the extended position. When the handle 338 is closed, the valve 394 is closed to prevent air from escaping from the cylinder 390 through the valve 394. Pressurized air from the cylinder 390 is passed via a transfer or an outlet tube 398 (see FIGS. 21 and 25) to a release valve assembly 400.

The release valve assembly 400 is in turn in communication with the TRANSJECTOR™ multi-flow ejector assembly 306 so that pressurized gas may be supplied to the open cavity 384 as previously described in FIG. 19. A seal 402 is provided between the valve assembly 400 and the TRANSJECTOR™ multi-flow ejector assembly 306 to prevent high pressure air supplied from the valve assembly 400 from escaping between the interface between the valve assembly 400 and the TRANSJECTOR™ multi-flow ejector assembly 306. The seal 402 is preferably constructed of urethane, silicone, or a similar elastomer, and is angled relative to a longitudinal axis of the TRANSJECTOR™ multi-flow ejector assembly 306. In this way, the TRANSJECTOR™ multi-flow ejector assembly 306 may easily be inserted and removed to and from the housing 302 while at the same time allowing for a sufficient interface seal.

The valve assembly 400 includes a valve stem 404 and a valve poppet 406 for selectively preventing air from flowing through the assembly 400 and will be described in greater detail hereinafter with reference to FIGS. 27–29. In FIGS. 21–24, the valve assembly 400 is shown in the open position, with the poppet 406 being unseated. In such a configuration, gas within the cylinder 390 will not be significantly compressed upon translation of the piston 388 since air within the cylinder 390 will escape through the outlet tube 398. When the valve assembly 400 is closed, air is prevented from escaping from the outlet tube 398 so that only a "full stroke" of air within the cylinder 390 may be compressed. In a particularly preferable aspect of the invention, the apparatus 300 is configured to close the valve assembly 400 as the piston 388 reaches the extended position so that air within the cylinder 390 may be compressed when the handle 338 is translated back toward the housing 302. To close the valve assembly 400 in this manner, the handle assembly 336 includes a linkage 408 (see FIG. 22) having rack 410 securely attached thereto. The rack 410 includes an elongate slot 412 for receiving a valve reset link 414 (see FIGS. 21 and 24). As best shown in FIGS. 21 and 24, the reset link 414 is pivotally attached to a roller cam 416. In turn, the roller cam 416 is pivotally attached to a valve release button 418.

As best shown in FIGS. 25 and 26, as the handle 338 is translated away from the housing 302 and as it reaches the fully extended position, the linkage 408 pivots about a pin 420 causing the reset link 414 to slide within the slot 412 until reaching a left-hand end of the slot 412. At this point, the reset link 414 is translated in the direction of the handle 338 to pivot the roller cam further about pin 422. Further translation of the handle 338 causes the roller cam 416 to lock over center. As the roller cam 416 toggles over center, the release button 418 is translated outward from the housing 302 and the valve stem 404 is driven upwards by the roller to seat the poppet 406 against a seat 452 (see FIG. 29), thereby closing the valve assembly 400. At the same time, the piston 388 is translated via linkage 392 to the extended position. As the handle 338 is translated back toward the housing 302, the reset link 414 slides within the slot 412 while the cam 416 remains over center to keep the valve assembly 400 closed. At the same time, the piston 388 is translated within the cylinder 390 to compress the air within the cylinder 390. When the operator is ready to produce the aerosolized medicament in the capture chamber 304, the release button 418 is depressed to move the cam 416 from over center and allow the valve assembly 400 to be opened.

In one particular aspect, the apparatus 300 may be configured to prevent translation of the handle 338 back toward the housing 302 until the handle 338 is fully extended to place the cam 416 over center and close the valve 400. To restrict movement of the handle 338 in this manner, the handle assembly includes an interlock pawl 424 (see FIG. 22) for engaging ratchet teeth 426 on the rack 410. As the handle 338 is extended to pivot the cam 416 about pin 422, the pawl 424 engages the teeth 426 of the rack 410 to prevent closure of the handle 338 until the cam 416 moves over center to close the valve assembly 400. An interlock pawl spring 425 is provided to bias the pawl 424 against the ratchet teeth 426 until the cam 416 is over center. In this way, pumping of the handle 338 is prevented which would prematurely deliver air into the TRANSJECTOR™ multi-flow ejector assembly 306. Such premature delivery is undesirable if the user has already loaded and punctured the receptacle. Alternatively, an interlock may be provided to prevent piercing of the receptacle 342 by the TRANSJECTOR™ multi-flow ejector assembly 306 until the valve assembly 400 is closed.

Figure 22:
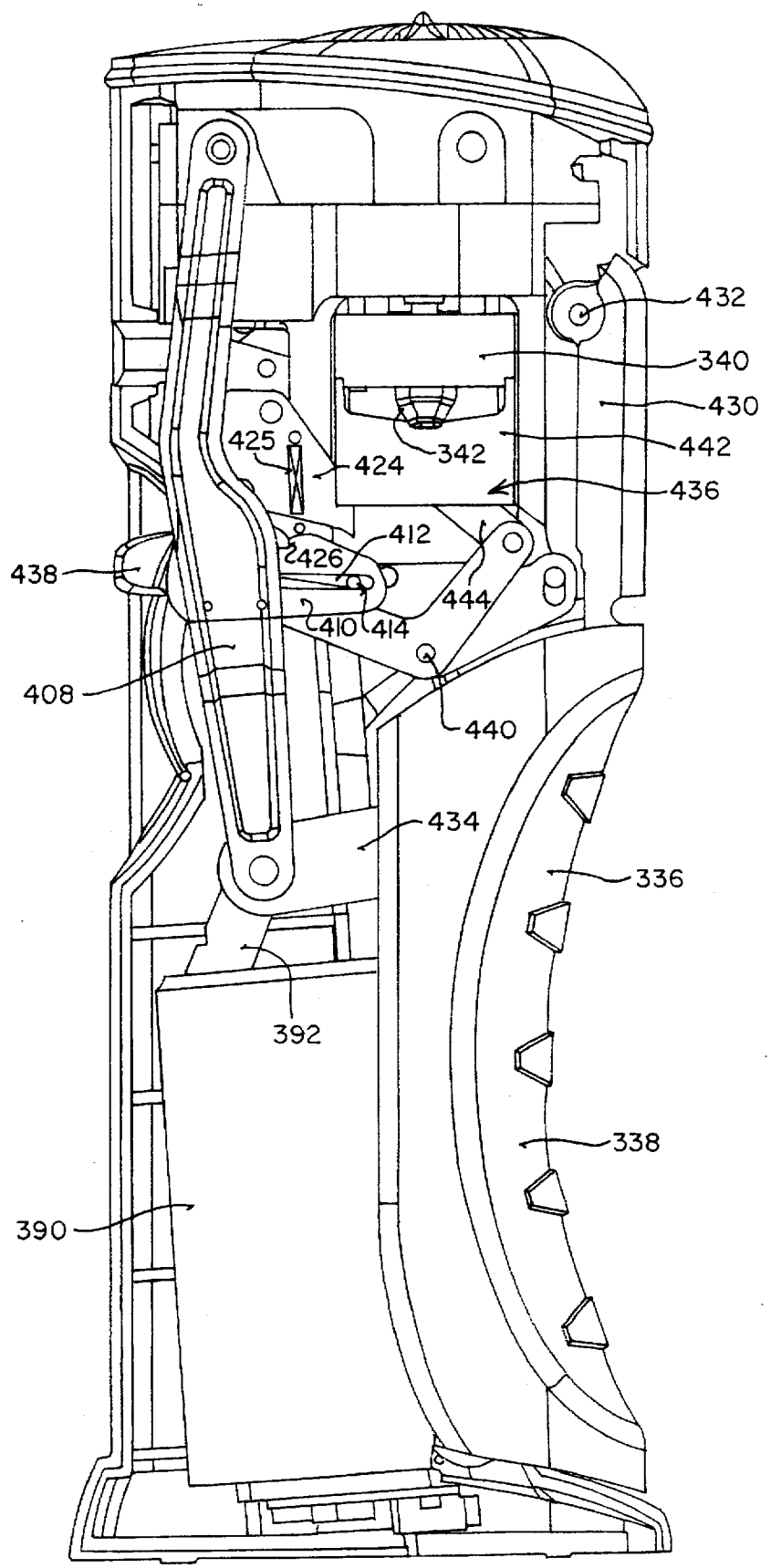
FIG. 22 is a side view of the apparatus of FIG. 13 having its outside cover removed.
Figure 25:
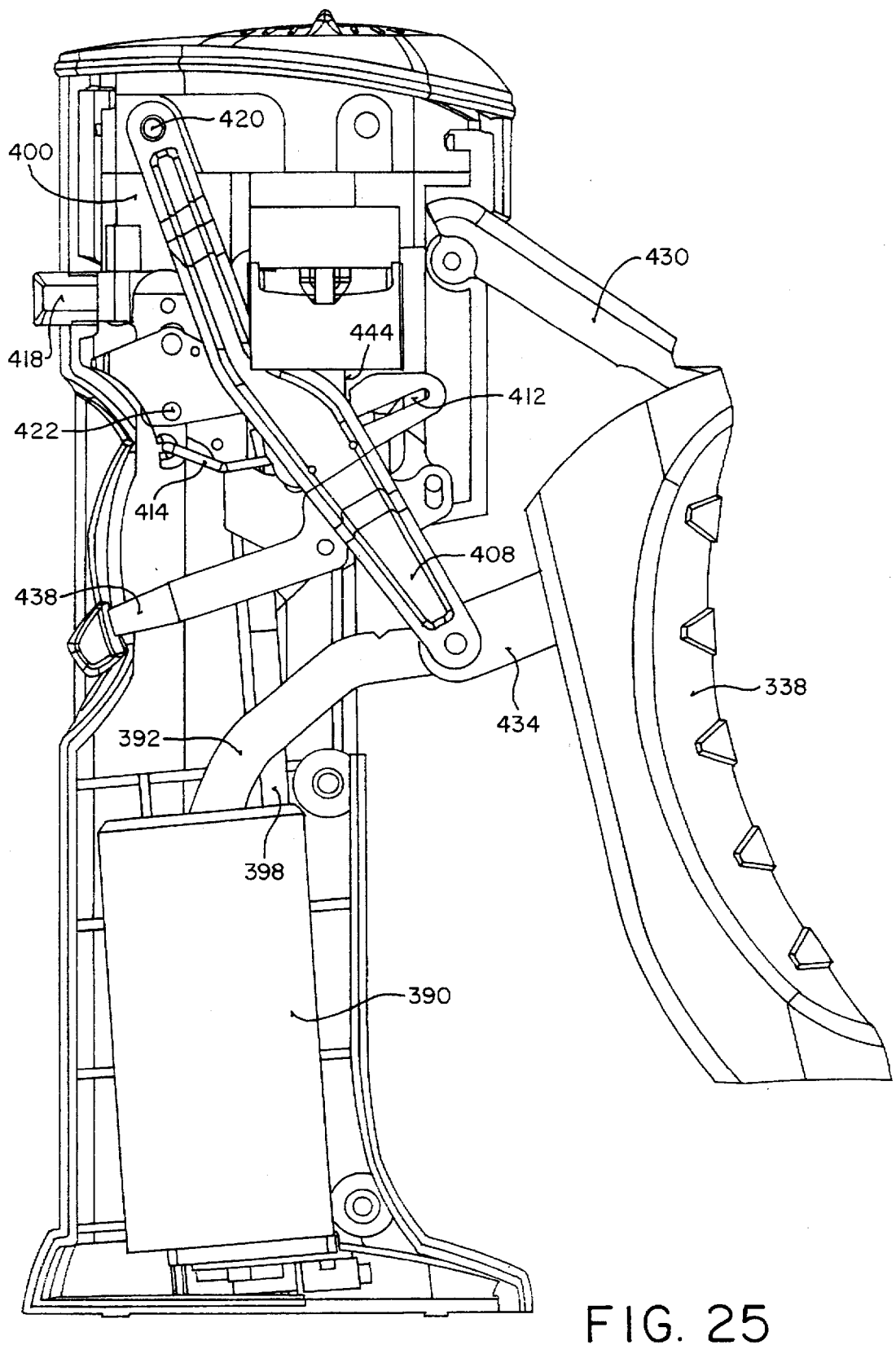
FIG. 25 illustrates the handle assembly and other selected components of FIG. 23, with the handle assembly being extended to close the release valve and retract a piston according to the present invention.
Figure 26:
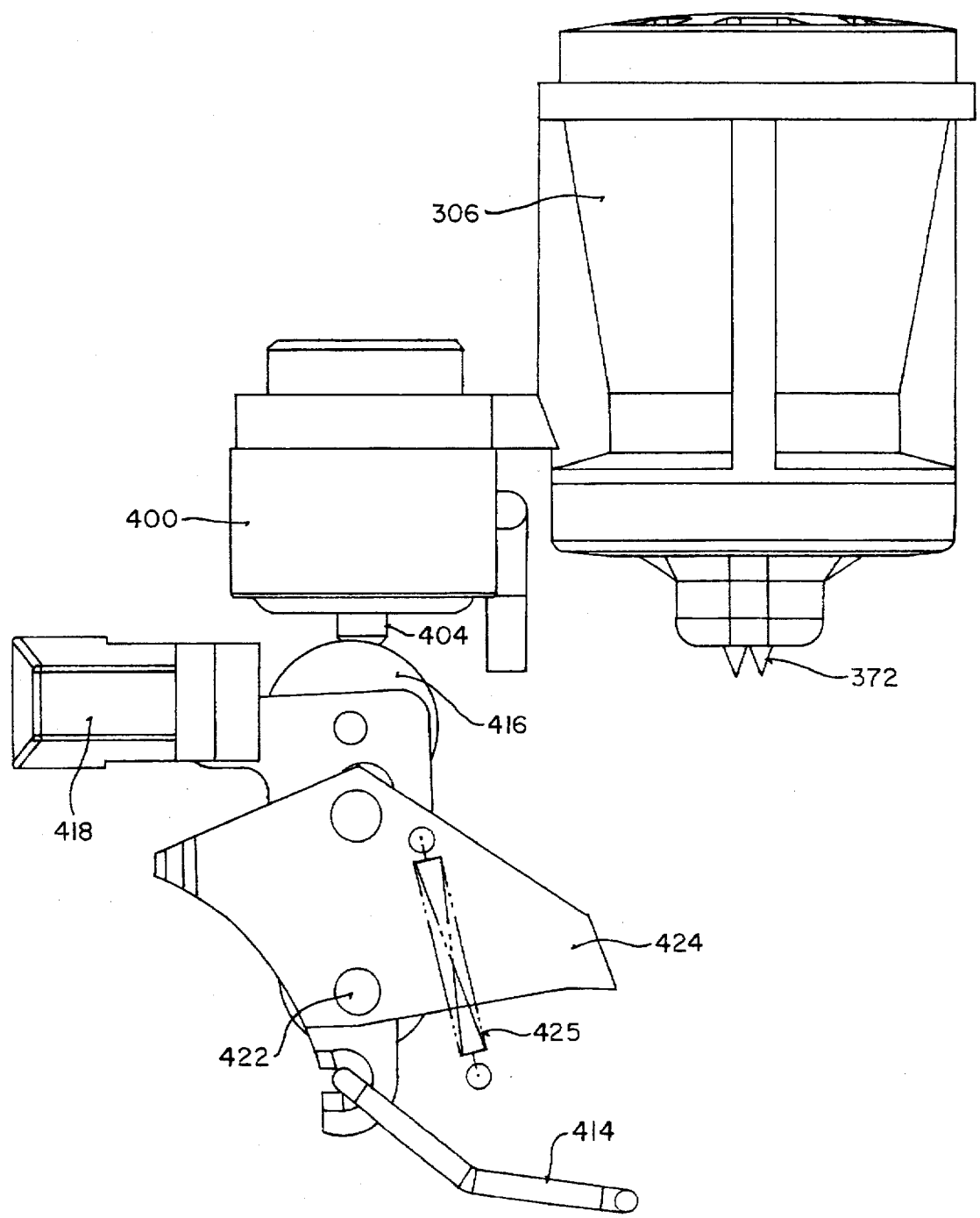
FIG. 26 is a more detailed view of the release valve of FIG. 25 shown in the closed position.

Referring to FIGS. 22 and 25, translation of the handle 338 relative to the housing 302 will be described in greater detail. The handle assembly 336 further includes a linkage 430 that is pivotally connected to the housing 302 by pin 432. Connecting the handle 338 to linkage 392 and linkage 408 is a linkage 434. Together, linkages 392, 408, 430 and 434 provide a four-bar linkage system which allow the handle 338 to be moved radially outward from the housing 302 with the handle 338 being maintained generally parallel to the housing 302. Further, when the valve assembly 400 is closed and the handle 338 is translated back toward the housing 302, a substantially uniform force is required over the handle's range of motion. In this way, as the user forces the handle 338 back toward housing 302 to compress the air in the cylinder 390, the user feels a generally equal resistive force during the entire compression step. Moreover, the maximum distance that the handle 338 is translated away from the housing 302 is reduced, thereby making it easier for smaller hand sizes to operate.

Figure 23:
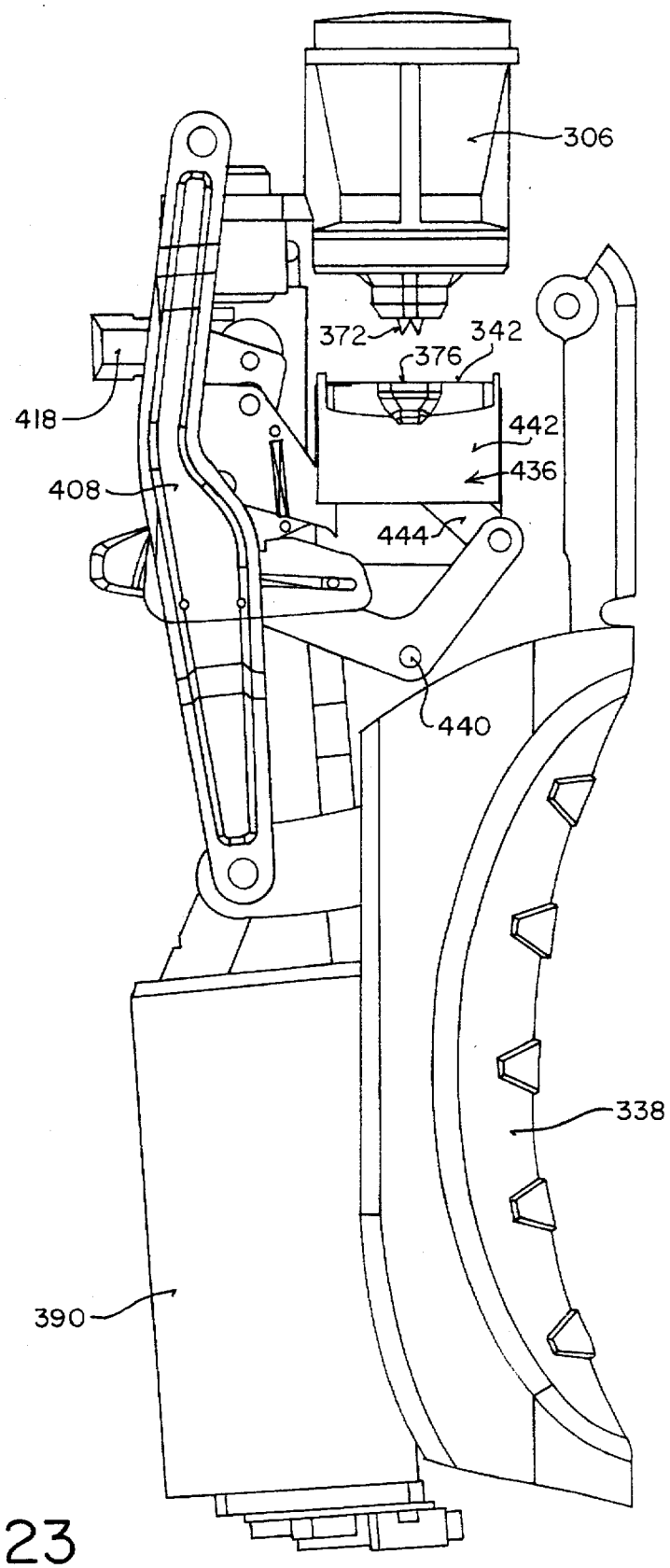
FIG. 23 is a side view of a handle assembly along with other selected components of the apparatus of FIG. 13, with the handle assembly being shown in a closed configuration.
Figure 24:
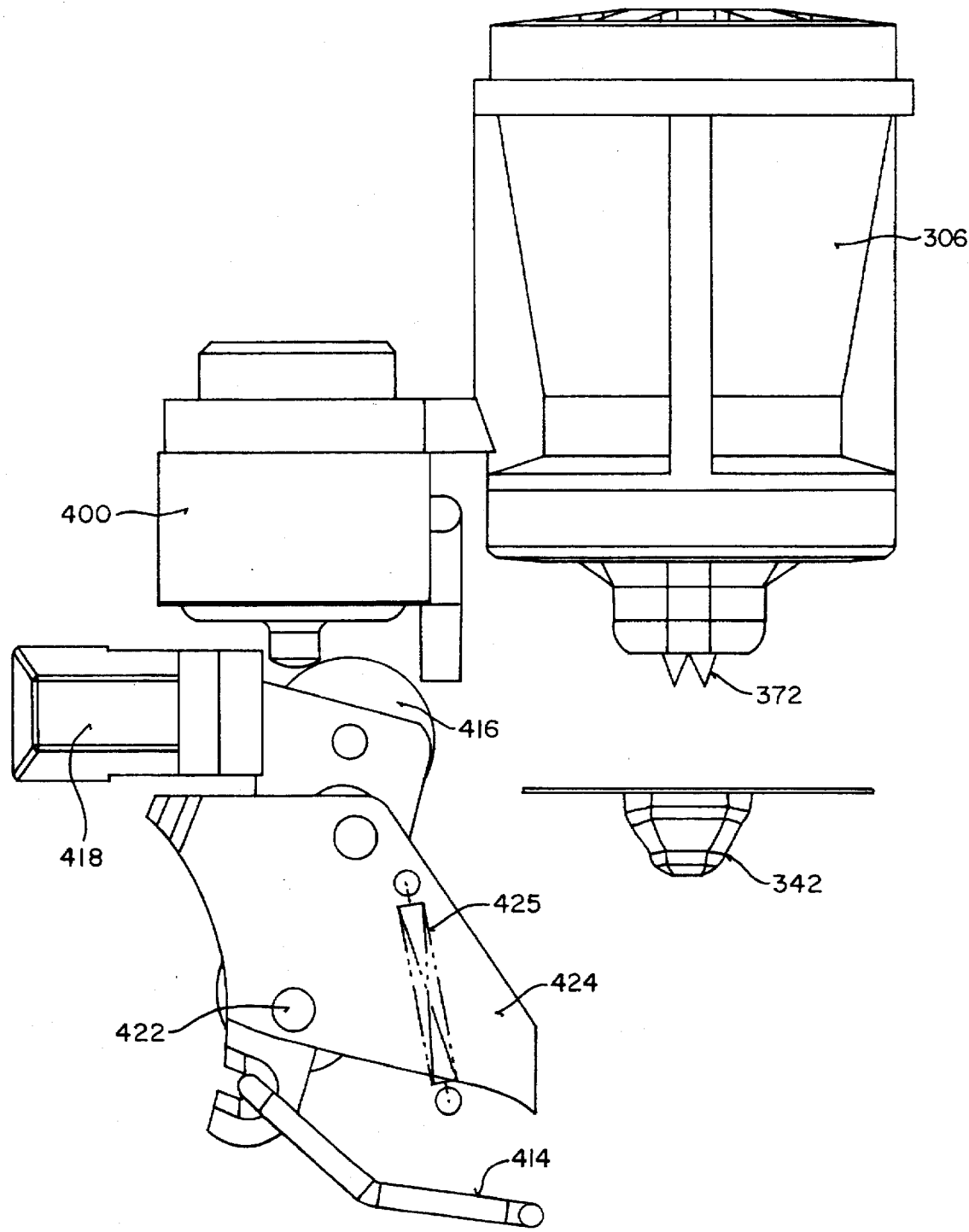
FIG. 24 is a more detailed view of selected components of the apparatus of FIG. 23 and shows a release valve in an open configuration.

As best shown in FIGS. 22 and 23, the apparatus 300 further includes a carriage assembly 436 for translating the receptacle 342 within the aperture 340 so that the penetrating element 370 and the penetrating structures 372 may pierce the lid 376 of the receptacle 342. The carriage assembly 436 includes a thumb toggle 438 that is pivotally connected to the frame of the housing 302 by a pin 440. The receptacle 342 is held within a carrier 442 which in turn is connected to the thumb toggle 438 by a linkage 444. Operation of the carriage assembly 436 is as follows. Initially, the receptacle 342 is inserted into the aperture 340 as previously described with the receptacle 342 resting on the carrier 442. The thumb toggle 438 is then depressed to pivot the toggle 438 about pin 440 and to lift the carrier 442 toward the TRANSJECTOR™ multi-flow ejector assembly 306. As best shown in FIG. 25, the thumb toggle 438 is depressed until the TRANSJECTOR™ multi-flow ejector assembly 306 pierces the lid on the receptacle 342 and the linkage 444 moves over center. When the linkage 444 is over center, the receptacle 342 is locked in place against the end gasket 368 of the TRANSJECTOR™ multi-flow ejector assembly 306 (see FIG. 25). Preferably, the carriage assembly 436 will be configured to compensate for overtravel of the carrier 442. In this way, the carrier 442 will be relaxed after the receptacle 342 has been pierced by the TRANSJECTOR™ multi-flow ejector assembly 306 but will still provide a sufficient seal between the TRANSJECTOR™ multi-flow ejector assembly 306 and the receptacle 342. To lower the carrier 442, the thumb toggle 438 is lifted to move the linkage 444 from over center. The receptacle 342 may then be removed from the aperture 340 by grasping the tab 380 and pulling the receptacle 342 from the aperture 340.

Figure 27:
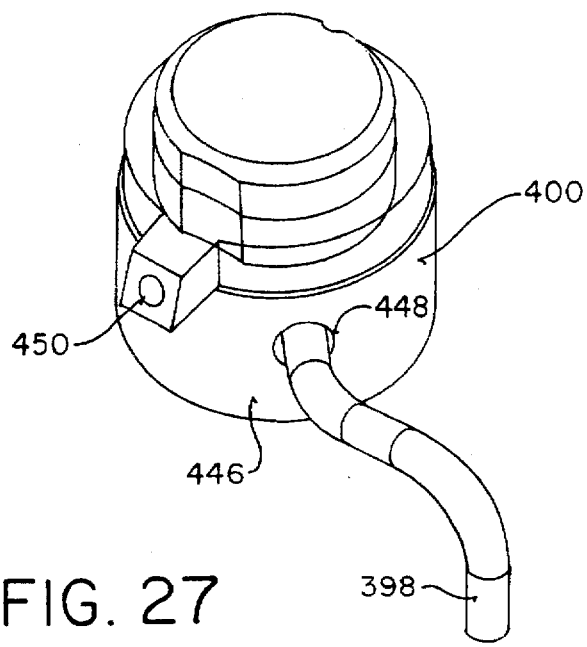
FIG. 27 is a perspective view of the release valve of the apparatus of FIG. 13.
Figures 28, 29:
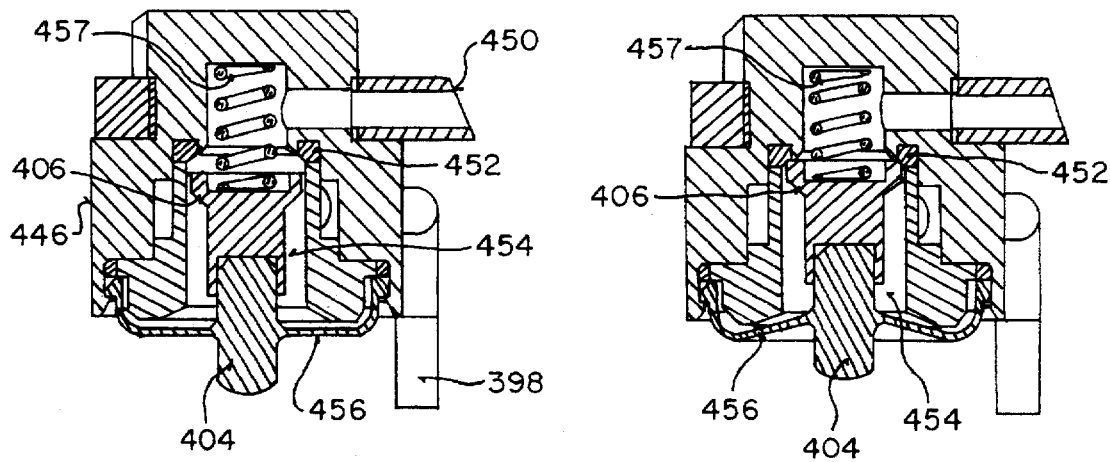
FIG. 28 is a cross-sectional view of the release valve of FIG. 27 showing the valve in an open configuration.
FIG. 29 is a cross-sectional view of the release valve of FIG. 27 with the valve being in a closed configuration.

Referring to FIGS. 27–29, construction of the release valve assembly 400 will be described in greater detail. The valve assembly 400 includes a casing 446 having an inlet port 448 and an outlet port 450. The outlet tube 398 which connects the cylinder 390 to the valve assembly 400 passes through the inlet port 448. The interface seal 402 is placed between the outlet port 450 and the TRANSJECTOR™ multi-flow ejector assembly 306 as previously described.

The valve assembly 400 is shown in the open state in FIG. 28. When open, the poppet 406 is spaced apart from an O-ring seat 452. The poppet 406 is held within a central chamber 454 which is sealed from the outside environment (except for the outlet port 450) by a diaphragm 456. When open, air introduced into the central chamber 454 from the outlet tube 398 freely passes around the poppet 406 and exits the outlet port 450. When closed (see FIG. 29), air introduced into the central chamber 454 from the outlet tube 398 forces the poppet 406 against the seat 452 which prevents escape of the compressed air from the central chamber 454. The valve assembly 400 is preferably configured so that the seal between the poppet 406 and the seat 452 will hold up to about 120 psi of pressure, and more preferably at about 80 psi.

To open the valve assembly 400, the release button 418 is depressed to move the cam 416 from over center and to allow the poppet 406 to be moved away from the seat 452. To force the poppet 406 away from the seat 452, a spring 457 is provided. The spring 457 will preferably be selected to provide a force sufficient to overcome the force on the opposite side of the poppet that is produced by the compressed air within the chamber 454. Hence, when the release button 418 is depressed, the spring 457 will overcome the force produced by the compressed air within the chamber 454 and will promptly force the poppet 406 away from the seat 452 and allow the valve to open. The valve will rapidly open to allow the compressed air in the cylinder 390 and tube 398 to almost instantaneously rush out the central chamber 454 through the outlet port 450 where it is delivered to the TRANSJECTOR™ multi-flow ejector assembly 306 as previously described. In this manner, the valve assembly 400 operates in a "snap" acting manner to provide a precise amount of gas to the TRANSJECTOR™ multi-flow ejector assembly 306 in a rapid, abrupt and irreversible manner so that the powder may be sufficiently aerosolized in a repeatable and a predictable manner.

Optionally, the housing 302 may further include an electronic memory chip along with a speaker 301 for providing audible instructions to a user regarding operation of the apparatus 300. The chip will preferably be an EPROM, PROM, or PAL chip having stored electronic information regarding operation of the apparatus 300 and will be configured to be actuated upon deployment of the capture chamber 304. In this way, as a user prepares for a treatment, audible instructions will be given. Preferable instructions include deployment of the chamber 304, charging of the apparatus with the handle assembly 336, breathing instructions, and the like, as well as other pertinent information as determined by the manufacturer.

Although the foregoing invention has been described in some detail by way of illustration and example, for purposes of clarity of understanding, it will be obvious that certain changes and modifications may be practiced within the scope of the appended claims.

What is claimed is:

1. An improved apparatus for aerosolizing a powdered medicament, the apparatus being of the type having a housing and a source of pressurized gas for aerosolizing the powdered medicament, wherein the improvement comprises:

a pressurization cylinder;

a piston slidable within the cylinder;

a release valve in communication with the cylinder; and a handle assembly having a handle operably attached to the piston and a valve closing mechanism operably attached to the handle, wherein movement of the handle in one direction moves the valve closing mechanism to engage and close the valve in a stable, closed position and movement of the handle in another direction axially translates the piston within the cylinder to produce the pressurized gas while the valve remains in the stable closed position to maintain the gas under pressure until released.

2. An improved apparatus as in claim 1, wherein the release valve comprises a valve stem connected to a valve popper, wherein the valve closing mechanisms comprises a roller cam adjacent the valve stem for translating the valve stem to close the valve as the handle is translated radially outward from the housing.

3. An improved apparatus as in claim 2, wherein the handle assembly further comprises a toggle link which moves over-center to hold the roller cam against the valve stem and keep the valve closed.

4. An improved apparatus as in claim 3, wherein the handle assembly further includes a linkage between the handle and the piston, wherein the linkage reciprocally translates the piston between a retracted position and a charged position within the cylinder as the handle is translated radially outward and radially inward relative to the housing.

5. An improved apparatus as in claim 4, further comprising an interlocking means for preventing inward radial translation of the handle until the toggle link has moved over-center.

6. An improved apparatus as in claim 5, wherein the interlocking means comprises a ratchet and a pawl.

7. An improved apparatus as in claim 3, further comprising a release button for translating the roller cam from the over-center position to open the valve.

8. An improved apparatus as in claim 4, wherein the cylinder includes a one-way valve for allowing air to enter the cylinder as the piston is translated to the retracted position.

9. An improved apparatus as in claim 1, wherein a powdered medicament is held within a receptacle, and further comprising a feed tube having an inlet end, an outlet end, and a lumen extending therebetween, wherein the inlet end may be inserted into the receptacle so that compressed gas exiting the release valve may be flowed past the outlet end, wherein powdered medicament from the receptacle is extracted through the tube and dispersed in the flowing compressed gas to form an aerosol.

10. An improved apparatus as in claim 9, further comprising means for piercing at least one hole in an access surface of the receptacle simultaneously with inserting the inlet end of the feed tube into the receptacle.

11. An improved apparatus as in claim 10, wherein the piercing means comprises a pair of penetrating structures, and wherein the penetrating structures are each disposed at an oblique angle relative to the access surface of the receptacle when the penetrating structures are pierced through the access surface.

12. An improved apparatus as in claim 11, further comprising means for reciprocally translating the receptacle toward and away from the piercing means.

13. An improved apparatus as in claim 12, wherein the translating means comprises an over-center linkage for locking the receptacle in place upon insertion of the inlet end of the feed tube into the receptacle.

14. An improved apparatus as in claim 13, further comprising a positioning pin for aligning the receptacle in a preferred orientation relative to the piercing means while inserting the inlet end of the feed tube into the receptacle.

15. An improved apparatus as in claim 1, wherein the handle assembly includes four linkages for attaching the handle to the housing, wherein the handle may be translated radially outward and radially inward relative to the housing with a generally constant force.

16. An improved apparatus as in claim 1, further comprising means on the housing for producing verbal operating instructions.

17. A receptacle for holding a powdered medicament, the receptacle being adapted to be received into an aperture in a housing of an aerosolizing apparatus, the receptacle comprising:

a receptacle body having a puncturable access surface, wherein the access surface is constructed of a material which will peel back when penetrated at an angle with a pointed structure; and a tab extending from the receptacle body, wherein the receptacle body may be received into the aperture with at least a portion of the tab remaining outside the housing, wherein the tab includes a keyed hole adapted to receive a keyed alignment pin in the aerosolizing apparatus.

18. An improved method for aerosolizing a powdered medicament, said method being of the type wherein the powder is entrained and suspended in a flowing gas stream, wherein the improvement comprises:

providing a housing having a pressurization cylinder, a piston slidable within the cylinder, a release valve in communication with the cylinder, and a handle operably engageable with the valve for axially translating the piston and for engaging and closing the release valve;

moving the handle away from the housing to axially translated the piston within the cylinder to a retracted position and to engage and close the release valve in a stable, closed position;

moving the handle back toward the housing to translate the piston to a charged position and create a pressurized gas while the valve remains in the stable, closed position to maintain the gas under pressure until separately released; and separately releasing the valve to abruptly discharge the pressurized gas.

19. An improved method as in claim 18, further comprising preventing translation of the handle in the direction of the housing until the release valve is closed.

20. An improved method as in claim 19, further comprising holding the release valve closed while translating the handle back toward the housing.

21. An improved method as in claim 18, wherein the handle is translated away from and toward the housing with the handle being generally parallel to the housing.

22. An improved method as in claim 18, further comprising supplying a generally constant force when translating the handle toward the housing when pressurizing the gas.

23. An improved method as in claim 18, further comprising introducing the powder that is suspended in the released gas into a capture chamber while simultaneously bleeding off a preselected amount of gas from the capture chamber.

24. An improved method as in claim 18, further comprising providing a multi-flow ejector assembly for receiving the pressurized gas and aerosolizing the powder, and periodically removing the multi-flow ejector assembly from the housing for cleaning.

25. An improved method as in claim 25, further comprising providing a receptacle having a puncturable lid for holding the medicament and translating the receptacle toward the multi-flow ejector assembly until the multi-flow ejector assembly penetrates the lid.

26. An improved method as in claim 20, further comprising guiding the receptacle toward the multi-flow ejector assembly so that the multi-flow ejector assembly penetrates the lid at a known and a predictable position.

27. An improved method as in claim 25, further comprising holding the receptacle with the multi-flow ejector assembly penetrating the lid until after the valve is released.

28. An improved method as in claim 18, further comprising producing verbal operating instructions from the housing.

29. A method for aerosolizing a powdered medicament, said method comprising:

providing receptacles having a receptacle body and a tab extending from the receptacle body, wherein the powdered medicament is held within the receptacle bodies;

inserting one receptacle into a housing having an aperture, wherein the receptacle body is received within the aperture and at least a portion of the tab remains outside the housing;

piercing the receptacle body and extracting the powdered medicament in a gas stream that can be inhaled;

pulling on the tab to remove the receptacle from the housing; and wherein the housing has a reciprocatable capture chamber for receiving the powder-bearing gas stream, and further comprising deploying the chamber prior to inserting the receptacle.

30. A method as in claim 29, wherein deploying the chamber exposes the aperture and wherein the chamber cannot be retracted until the receptacle is removed.

31. An improved apparatus for aerosolizing a powdered medicament, the apparatus being of the type having a housing and a source of pressurized gas for aerosolizing the powdered medicament, wherein the improvement comprises:

a pressurization cylinder;

a piston slidable within the cylinder;

a release valve in communication with the cylinder; and a handle assembly having a handle operably attached to the piston and a means for closing the valve, wherein movement of the handle closes the valve and axially translates the piston within the cylinder to produce the pressurized gas;

wherein the handle assembly includes four linkages for attaching the handle to the housing, wherein the handle may be moved radially outward and radially inward relative to the housing with a generally constant force.

32. An improved method for aerosolizing a powdered medicament, said method being of the type wherein the powder is entrained and suspended in a flowing gas stream, wherein the improvement comprises:

providing a housing having a pressurization cylinder, a piston slidable within the cylinder, a release valve in communication with the cylinder, and a handle for axially translating the piston and for closing the release valve;

moving the handle away from the housing to axially translate the piston within the cylinder to a retracted position and to close the release valve;

moving the handle back toward the housing to translate the piston to a charged position and create a pressurized gas wherein the handle resists the movement toward the housing with a generally constant resistive force;

releasing the valve to abruptly discharge the pressurized gas; and supplying a generally constant force when moving the handle toward the housing when pressurizing the gas.

* * * * *